(12) United States Patent
Park et al.

(10) Patent No.: US 10,590,385 B2
(45) Date of Patent: Mar. 17, 2020

(54) METHOD OF PRODUCING NATURAL KILLER CELLS AND COMPOSITION FOR TREATING CANCER

(71) Applicant: NKMAX Co., Ltd., Gyeonggi-do (KR)

(72) Inventors: Sang Woo Park, Gyeonggi-do (KR); Yong Man Kim, Gyeonggi-do (KR); Jae Seob Jung, Gyeonggi-do (KR); Yong-Hee Rhee, Gyeonggi-do (KR)

(73) Assignee: NKMAX CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/523,964

(22) Filed: Jul. 26, 2019

(65) Prior Publication Data

US 2019/0345449 A1 Nov. 14, 2019

Related U.S. Application Data

(63) Continuation of application No. PCT/US2019/016076, filed on Jan. 31, 2019.

(30) Foreign Application Priority Data

| Feb. 1, 2018 | (KR) | 10-2018-0012938 |
| Feb. 1, 2018 | (KR) | 10-2018-0012942 |
| Jan. 7, 2019 | (KR) | 10-2019-0001981 |
| Jan. 7, 2019 | (KR) | 10-2019-0001983 |

(51) Int. Cl.

| C12N 5/0783 | (2010.01) |
| A61K 35/17 | (2015.01) |
| A61K 38/20 | (2006.01) |
| A61P 35/00 | (2006.01) |

(52) U.S. Cl.
CPC ............ *C12N 5/0646* (2013.01); *A61K 35/17* (2013.01); *A61K 38/2013* (2013.01); *A61P 35/00* (2018.01); *C12N 2501/105* (2013.01); *C12N 2501/125* (2013.01); *C12N 2501/22* (2013.01); *C12N 2501/2302* (2013.01); *C12N 2501/2304* (2013.01); *C12N 2501/2307* (2013.01); *C12N 2501/2315* (2013.01); *C12N 2501/2318* (2013.01); *C12N 2501/2321* (2013.01); *C12N 2501/24* (2013.01); *C12N 2501/26* (2013.01); *C12N 2502/1114* (2013.01)

(58) Field of Classification Search
None
See application file for complete search history.

(56) References Cited

U.S. PATENT DOCUMENTS

| 9,175,266 | B2 | 11/2015 | Peled et al. |
| 9,938,498 | B2 | 4/2018 | Lee et al. |
| 2004/0173778 | A1 | 9/2004 | Roncarolo et al. |
| 2008/0166326 | A1 | 7/2008 | Lowdell |
| 2011/0135687 | A1 | 6/2011 | Koelle et al. |
| 2014/0120072 | A1 | 5/2014 | Yonemitsu et al. |
| 2014/0369955 | A1 | 12/2014 | Markovic et al. |
| 2015/0152387 | A1* | 6/2015 | Lee ..................... C12N 5/0646 424/93.71 |
| 2018/0010087 | A1 | 1/2018 | Miltenyi et al. |
| 2018/0057795 | A1 | 3/2018 | Childs et al. |
| 2018/0245044 | A1* | 8/2018 | Granzin ............... C12N 5/0646 |
| 2019/0153389 | A1* | 5/2019 | Fischkoff ............. C12N 5/0646 |

FOREIGN PATENT DOCUMENTS

| KR | 1020120016427 | 2/2012 |
| WO | WO 2006/050270 A2 | 5/2006 |
| WO | WO 2008/118369 A2 | 10/2008 |
| WO | WO 2017/037083 A1 | 1/2014 |
| WO | WO 2017/196657 A1 | 11/2017 |
| WO | WO 2018/161026 A1 | 9/2018 |

OTHER PUBLICATIONS

Burns et al., "IL-2-based immunotherapy after autologous transplantation for lymphoma and breast cancer induces immune activation and cytokine release: a phase I/II trail", Bone Marrow Transplantation (2003) 32, 177-186.
Denman et al., "Membrane-Bound IL-21 Promotes Sustrained Ex Vivo Proliferation of Human Natural Killer Cells", PLoS ONE 7(1), Jan. 18, 2019 in 13 pages.
Fujisaki et al., "Expansion of Highly Cytotoxic Human Natural Killer Cells for Cancer Cell Therapy." Expansion of Highly Cytotoxic NK Cells, American Association for Cancer Research, 69: (9), May 1, 2009, in 8 pages.
Granzin et al., "Highly efficient IL-21 and feeder cell-driven ex vivo expansion of human NK cells with therapeutic activity in a xenograft mouse model of melanoma", Oncoimmunology 2016, vol. 5, No. 9 in 11 pages.
Iyengar et al., "Purification of Human Natural Killer Cells Using a Clinical-Scale Immunomagnetic Method", international Society for Cellular Therapy, Cytotherapy, vol. 5, No. 6, 2003, 479-484.
Kloess et al., "Optimization of human NK cell manufacturing: Fully-automated separation, improved ex vivo expansion using IL-21 with autologous feeder cells and generation of anti-CD123-CAR-expressing effector cells", Human Gene Therapy, Mary Ann Liebert, Inc., 2017, in 43 pages.
Lang et al., "Clinical Scale Isolation of T Cell-depleted CD56+ Donor Lymphocytes in Children", Bone Marrow Transplantation (2002) 29, 497-502, in 6 pages.
Miller et al., "Successful Adoptive Transfer and in Vivo Expansion of Human Haploidentical NK Calls in Cancer Patients", American Society of Hematology, 2005 in 33 pages.

(Continued)

*Primary Examiner* — Daniel C Gamett
(74) *Attorney, Agent, or Firm* — Knobbe, Martens, Olson & Bear, LLP

(57) ABSTRACT

A method for producing natural killer cells is disclosed. The method comprises isolating peripheral blood mononuclear cells (PBMCs) from a blood sample; isolating at least one of CD56+ cells and/or CD3−/CD56+ cells from the PBMCs; and co-culturing the at least one of CD56+ cells and/or CD3−/CD56+ cells with a combination of feeder cells in the presence of a cytokine. A composition for treating cancer is also disclosed. The composition comprises the CD56+ natural killer cells produced by the disclosed method and a cytokine.

18 Claims, 17 Drawing Sheets

(56) References Cited

OTHER PUBLICATIONS

Passweg et al., "Purified donor NK-lymphocyte infusion to consolidate engraftment after haploidentical stem cell transplantation"Nature Publishing Group, Leukemia 18, 2004, 1835-1838.
Rosenberg et al , "Natural Killer Cells Plus IL-2 Following Chemotherapy to Treat Advanced Melanoma or Kidney Cancer" ClinicalTrials.gov: NCT00328861, May 22, 2006 in 10 pages.
Wendt et al., "Interleukin-21 Differentially Affects Human Natural Killer Cell Subsets", The Authors Journal compilation, 2007 Blackwell Publishing Ltd, Immunology, 122, 486-495.
Liu et al. "Growth and Activation of Natural Killer Cells Ex Vivo from Children with Neuroblastoma for Adoptive Cell Therapy," Clinical Cancer Research, Apr. 15, 2014, vol. 19, Issue 8, pp. 232-2143 (entire document).
Rubnitz et al., "NKAML: A Pilot Study to Determine the Safety and Feasibllity of Haploidentical Natural Killer Cell Transplantation in Childhood Acute Myelold Leukema," Journal of Clinical Oncology, Feb. 20, 2010, vol. 28, No. 6, pp. 955-959 (entire document).
International Search Report and Written Opinion; PCT/US2019/016076; dated Apr. 25, 2019, in 15 pages.
International Search Report dated Jul. 29, 2013 for International Patent Application No. PCT/KR2013/003981 in 5 pages.
Written Opinion dated Jul. 29, 2013 for International Patent Application No. PCT/KR2013/003981 in 6 pages.
Allan et al., "The role of 2 FOXP3 isoforms in the generation of human CD4+ Tregs", *J. Clin. Invest.* 115:3276-3284 (2005).
Joao F. Lacerda et al., "Human Epstein-Barr Virus (EBV)-specific Cytotoxic T Lymphocytes Home Preferentially to and Induce Selective Regressions of Autologous EBV-induced B Cell Lymphoproliferations in Xenografted C.B-17 Seid/Seid Mice", J. Exp. Med, 183:1215-1228, (1996).
Motohashi, S. et al., "A Phase I Study of in vitro Expanded Natural Killer T Cells in Patients with Advanced and Recurrent Non-Small Cell Lung Cancer," Clinical Cancer Research, Oct. 15, 2006, 6079-6086, vol. 12, Issue 20, American Association for Cancer Research.
Numbenjapon et al., "Antigen-independent and antigen-dependent methods to numerically expand CD19-specific $CD8_+T$ cells". Experimental Hematology 35 (2007) 1083-1090.
Tai et al., "CD28 costimulation of developing thymocytes induces Foxp3 expression and regulatory T cell differentiation independently of interleukin 2" *Nature Immunology*, vol. 6, No. 2, pp. 152-162 (2005).
Turtle et al., "Artificial antigen presenting cells for use in adoptive immunotherapy", NIH Public Access, Author Manuscript, *Cancer J.* Author manuscript; available in PMC Jul. 1, 2011, Published in final edited form as: *Cancer J.* 2010 ; 16(4): 374-381.
Koehl et al., "IL-2 activated NK cell immunotherapy of three children after haploidentical stem cell transplantation", Blood Cells Mol Dis 2004; 33:261-6.
Klingemann et al., "Ex vivo expansion of natural killer cells for clinical applications", Cytotherapy 2004; 6:15-22.
Berg et al., "Clinical-grade ex vivo-expanded human natural killer cells up-regulate activating receptors and death receptor ligands and have enhanced cytolytic activity against tumor cells", Cytotherapy 2009; 11:341-55.
Granzin et al., "Fully automated expansion and activation of clinical-grade natural killer cells for adoptive immunotherapy", Cytotherapy 2015; 17:621-32.
Childs et al., "Bringing natural killer cells to the clinic: ex vivo manipulation", Hematology Am Soc Hematol Educ Program 2013; 2013:234-46.
Park et al., "Gene expression analysis of ex vivo expanded and freshly isolated NK cells from cancer patients", J Immunother 33(9): 945-955 (2010).
Granzin et al., "Highly efficient IL-21 and feeder cell-driven ex vivo expansion of human NK cells with therapeutic activity in a xenograft mouse model of melanoma", Oncoimmunology 2016; Aug. 5;5(9):e1219007.

* cited by examiner

FIG. 14

METHOD OF PRODUCING NATURAL KILLER CELLS AND COMPOSITION FOR TREATING CANCER

INCORPORATION BY REFERENCE TO ANY PRIORITY APPLICATIONS

This application is a continuation application of International Patent Application No. PCT/US2019/016076, filed Jan. 31, 2019, which claims the benefit of Korean Patent Application No. KR-10-2018-0012938, filed Feb. 1, 2018, Korean Patent Application No. KR-10-2018-0012942, filed Feb. 1, 2018, Korean Patent Application No. KR-10-2019-0001981, filed Jan. 7, 2019, and Korean Patent Application No. KR-10-2019-0001983, filed Jan. 7, 2019, the disclosures of which are hereby incorporated by reference in their entireties.

BACKGROUND

Field

The present disclosure relates to a manufacturing method for high-purity natural killer cells.

Description of the Related Art

The human body is protected from pathogens by an immune response, coordinated by the immune system, which is composed of many immune-related cells, chemical mediators, such as cytokines, and the like. Leukocytes, especially lymphocytes, play an important role in such an immune system. Lymphocytes are involved in both innate and acquired immunity.

Natural killer cells (NK cells) are one type of innate immune cells, which are known to non-specifically kill cancer, recognize and kill viruses, bacteria, and the like, and kill pathogens with enzymes such as perforin and granzyme or by Fas-FasL interaction. In the case of cancer patients, it has been reported that a decrease in cancer cell cytotoxicity of these NK cells is associated with the onset of various types of cancer, such as lung cancer (Carrega P., et al., Cancer, 2008: 112: 863-875), liver cancer (Jinushi M, et al., J Hepatol., 2005: 43; 1013-1020), breast cancer (Bauernhofer T, et al., Eur J Immunol. 2003: 33; 119-124), uterine cancer (Mocchegiani E., et al., Br j Cancer., 1999: 79: 244-250), blood cancer (Tajima F., et al, Leukemia 1996: 10:478-482), and the like. Accordingly, for cancer therapy, it is desirable Jo increase the cancer cell cytotoxicity of the NK cells.

In order to obtain the therapeutic effect of NK-mediated killing of the cancer cells, a large amount of NK cells having high purity is required, but it is not easy to obtain a large amount of blood from the cancer patient, and of the proportion of NK cells in the blood is small only about 5 to 20%. Thus, it has been difficult for using the NK cells as an immunotherapeutic agent.

As a result, it is desirable to effectively expand and proliferate only the NK cells, but in a conventional method of proliferating NK cells, various expensive cytokines need to be used at a high concentration, thus the corresponding therapy is only available to some financially stable patients. Further, according to conventional methods of proliferating NK cells, other types (e.g., T cells, B cells, etc.) of immune cells may be present together with the NK cells, and allogenic administration of the NK cells containing T cells may cause a graft versus host disease (GVHD) and allogenic administration of the NK cells containing B cells to blood-type incompatible subjects may cause a passenger B-lymphocyte syndrome, and thus, the anti-cancer effect is not maximized.

Further, in addition to expanding and proliferating NK cells, it is desirable to highly maintain the functions of NK cells until the expanded and proliferated NK cells are actually used. As a result, the development of a composition capable of promoting the proliferation of the NK cells, increasing production of cytokines such as TNF-, INF- and GM-CSF derived from the NK cells, and increasing cancer cell cytotoxicity of the NK cells is sought.

SUMMARY

This application is related to methods of producing high-purity natural killer cells, and a cell therapeutic composition for treating cancer comprising high-purity natural killer cells and cytokines. Any features, structures, or steps disclosed herein can be replaced with or combined with any other features, structures, or steps disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

In an embodiment, a method of producing natural killer cells is disclosed. The method includes: isolating peripheral blood mononuclear cells (PBMCs) from a blood sample; isolating at least one of CD56+ cells and/or CD3−/CD56+ cells from the PBMCs; and co-culturing the at least one of CD56+ cells and/or CD−/CD56+ cells with a combination of feeder cells in the presence of a cytokine.

In certain embodiments, isolating at least one of CD56+ cells and/or CD3−/CD56+ cells from the PBMCs is conducted by using at least one of CD56 microbeads and CD3 microbeads. In certain embodiments, the cytokine is selected from a group consisting of IL-2, IL-21, IL-15, Flt3-L, SCF, IL-7, IL-18, IL-4, type I interferons, GM-CSF, IGF 1, and combinations thereof. In certain embodiments, the cytokine may be added at a concentration of 50-1000 IU/mL.

In certain embodiments, the combination of feeder cells includes irradiated Jurkat cells and irradiated Epstein-Barr virus transformed lymphocyte continuous line (EBV-LCL) cells. In a variation, the ratio of the irradiated Jurkat cells and the irradiated EBV-LCL cells may be about 1:0.1-5. Each of the irradiated Jurkat cells and the irradiated EBV-LCL cells may be obtained by irradiation of 50-500 Gy.

In certain embodiments, the co-culturing may include co-culturing for 1-50 days.

In certain embodiments, the method may further include co-culturing the at least one of CD56+ cells and/or CD3−/CD56+ cells with a combination of feeder cells, in the presence of a first cytokine for a first period; and subsequently co-culturing the at least one of CD56+ cells and/or CD3−/CD56+ cells with the combination of feeder cells, in the presence of a second cytokine for a second period. In a variation, the second cytokine may be added once or more during Day 0-6 of the second period. The second cytokine may be added once or more during the first six days of every fourteen-day cycle during the second period. The first cytokine may be IL-2. The second cytokine may be IL-21. The second cytokine may be added at a concentration of 10-100 ng/mL.

In certain embodiments, the at least one of CD56+ cells and/or CD3−/CD56+ cells and the combination of feeder cells is co-cultured with a ratio of about 1:1-100 of CD56+ cells and/or CD3−/CD56+ cells to feeder cells.

In certain embodiments, a composition made by the method is disclosed.

In an embodiment, a composition for treating cancer in a patient in need thereof is disclosed. The composition includes: an effective amount of CD56+ natural killer cells derived from peripheral blood, wherein the effective amount is in a range of about $1 \times 10^6$ to $5 \times 10^8$ cells per kg of the patient's body weight, and wherein the CD56+ natural killer cells are at least about 90% pure; IL-2 having a concentration of 50-50,000 IU/mL; and a pharmaceutically acceptable carrier.

In certain embodiments, the cytokine may be selected from a group consisting of IL-2, IL-21, IL-15, Flt3-L, SCF, IL-7, IL-18, IL-4, type I interferons, GM-CSF, IGF 1, and combinations thereof. In a variation, the cytokine may be IL-2. The cytokine may have a concentration of 50-50,000 IU/mL.

In certain embodiments, the cancer is selected from a group consisting of: blood cancer, stomach cancer, pancreatic cancer, cholangiocarcinoma, colon cancer, breast cancer, liver cancer, ovarian cancer, lung cancer, kidney cancer, prostate cancer and neuroblastoma.

In certain embodiments, the composition includes less than about 1% T cells.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 14 illustrates photographs of remaining AGS cells treated with NK cells treated with or without IL-2.

DETAILED DESCRIPTION

Figure 1A:
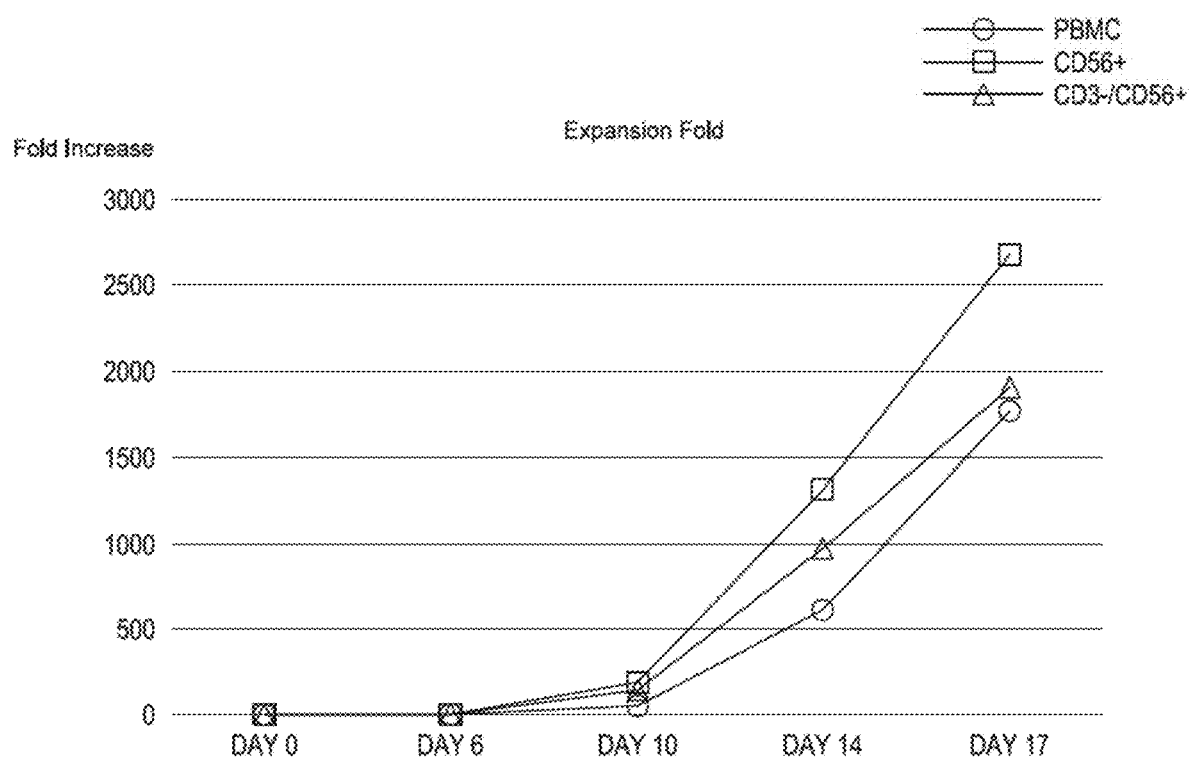
FIG. 1A illustrates a graph showing cell growth rates of NK cells produced from PBMCs, CD56+ cells, and CD3−/CD56+ cells.

A method for producing high-purity NK cells without using expensive cytokines has been developed by the inventors. The inventors found that, after CD56+ cells are isolated from peripheral blood mononuclear cells, when the CD56+ cells isolated from peripheral blood mononuclear cells are co-cultured with feeder cells in the presence of cytokines, high-purity CD56+ NK cells could be produced. Also, the present inventors have developed a cell therapeutic composition for treating cancer comprising NK cells which are effectively usable for allogenic therapy. As a result, the inventors found that when a specific cytokine was added to CD56+ NK cells isolated from peripheral blood mononuclear cells, high survival rate and high anti-cancer activity were exhibited. Therefore, the inventors sought to develop a method for expanding NK cells and to provide a cell therapeutic composition for the treatment of cancer comprising expanded peripheral blood-derived CD56+ NK cells together with cytokines.

According to some embodiments, a method for producing high-purity NK cells may include: isolating peripheral blood mononuclear cells (PBMCs) from a blood sample ("First Isolation Step"); isolating cells selected from a group consisting of CD56+ cells and CD3−/CD56+ cells from the peripheral blood mononuclear cells ("Second Isolation Step"); and co-culturing the cells selected from a group consisting of CD56+ cells and CD3−/CD56+ cells together with feeder cells in the presence of cytokine ("Culturing Step"). Each step is described in greater detail herein. The CD3−/CD56+ cells produced according to the disclosed method may exhibit not only higher purity and higher anti-cancer activity, but also other distinguished characteristics, such as having different surface markers or activated receptors, for example, one or more from CD16, CD25, CD27, CD28, CD69, CD94/NKG2C, CD94/NKG2E, CD266, CD244, NKG2D, KIR2S, KIR3S, Ly94D, NCRs, IFN-a, IFN-b, CXCR3, CXCR4, CX3CR1, CD62L and CD57, as compared with NK cells produced from peripheral blood mononuclear cells without isolating CD56+ cells.

First Isolation Step

In the present specification, the "blood sample" may be, but not limited to, whole blood of the peripheral blood or leukocytes isolated from the peripheral blood using leukapheresis. Further, the peripheral blood may be obtained from a normal person, a patient having a risk of cancer, or a cancer patient, but the source of the peripheral blood is not limited thereto.

In the present specification, the term "leukapheresis" may refer to a method of selectively removing (isolating) leukocytes from the collected blood and then giving the blood to a patient again, and in some embodiments, the leukocytes isolated by the method may be used without additional methods such as a Ficoll-Hypaque density gradient method.

In the present specification, the term "peripheral blood mononuclear cell" may be used interchangeably with "PBMC", "mononuclear cell" or "monocyte", and may refer to a mononuclear cell isolated from the peripheral blood which is generally used for anti-cancer immunotherapy. The peripheral blood mononuclear cells may be obtained from the collected human blood using known methods such as a Ficoll-Hypaque density gradient method.

In some embodiments, the peripheral blood mononuclear cells may be autologous, but allogenic peripheral blood mononuclear cells may also be used for producing high-purity NK cells for anti-cancer immunotherapy according to methods described herein. Further, in some embodiments, the peripheral blood mononuclear cells may be obtained from a normal person, but the peripheral blood mononuclear cells may be also obtained from a patient having a risk of cancer and/or a cancer patient.

In the present specification, the term "CD56+ cells" may be used interchangeably with "CD56+ NK cells", or "CD56+ natural killer cells", and the term "CD3−/CD56+ cells" may be used interchangeably with "CD3−/CD56+ NK cells." The CD56+ cells or CD3−/CD56+ cells may include cells in which CD56 glycoprotein on the cell surface is expressed, or further, cells in which CD3 glycoprotein is not expressed while the CD56 glycoprotein is expressed. Even the same type of immune cells may have differences in CD type attached to the cell surface and expression rate and thus, the functions thereof may be different.

Second Isolation Step

In some embodiments, the isolating of the CD56+ natural killer cells from the blood sample may be performed by an isolating method using at least one selected from the group consisting of CD56 microbeads and CD3 microbeads, or an isolating method using equipment such as CliniMACSs, a flow cytometry cell sorter, etc.

For example, the isolating method using the CD56 microbeads and/or the CD3 microbeads may be performed by adding the CD56 microbeads to PBMCs and then removing non-specific binding, or performed by adding the CD3 microbeads to the PBMCs to remove specific binding and then adding the CD56 microbeads again to remove non-specific binding. In some instances, through isolating CD56+ cells and/or CD3−/CD56+ cells from PBMCs, T cells or other non-natural killer cells may be removed.

Culturing Step

In the present specification, the term "cytokine" may refer to an immunoactive compound that is usable to induce the peripheral blood mononuclear cells to differentiate into NK cells.

In some embodiments, the cytokine may be interleukin-2 (IL-2), IL-15, IL-21, FMS-like tyrosine kinase 3 ligand (Flt3-L), a stem cell factor (SCF), IL-7, IL-18, IL-4, type I interferons, a granulocyte-macrophage colony-stimulating factor (GM-CSF), and an insulin-like growth factor 1 (IGF 1), but not limited thereto.

In some embodiments, the cytokine may be used at a concentration of 50-1,000, 50-900, 50-800, 50-700, 50-600, 50-550, 100-550, 150-550, 200-550, 250-550, 300-550, 350-550, 400-550, 450-550 IU/mL. Conventional methods of proliferating NK cells utilize high concentrations of various cytokines. Conversely, in some embodiments of the method of proliferating NK cells described herein, since two types of feeder cells may be used with the high-purity CD56+ cells, NK cells with high yield and high purity may be proliferated using only low concentrations of one cytokine.

In the present specification, the term "feeder cell" may refer to a cell that does not divide and proliferate, but has metabolic activity to produce various metabolites and thus, helps the proliferation of target cells.

In some embodiments, the feeder cells may be at least one selected from the group consisting of irradiated Jurkat cells, irradiated Epstein-Barr virus transformed lymphocyte continuous line (EBV-LCL) cells, and PBMC, HFWT, RPMI 1866, Daudi, MM-170, K562 or cells genetically modified by targeting K562 (for example, K562-mbIL-15-41BB ligand). For example, in one embodiment, the feeder cells may be the irradiated Jurkat cells and the EBV-LCL cells.

In the present specification, the term "Jurkat cell" or "Jurkat cell line" may refer to a blood cancer (immortalized acute T cell leukemia) cell line, which has been developed by Dr. Arthur Weiss of the University of California at San Francisco. Jurkat cells, in which various chemokine receptors are expressed and capable of producing IL-2, have not generally been considered as a possible candidate of the feeder cells for anti-cancer immunotherapy because MHC class I, which is a natural killer cell activation inhibitor, is highly expressed on the cell surface thereof. The Jurkat cells may be obtained from the ATCC (ATCC TIB-152).

In the present specification, the term "EBV-LCL cell" or "EBV-LCL cell line" refers to an Epstein-Barr virus transformed lymphocyte continuous Line (EBV-LCL) (D. M. Koelle et al., J Clin invest, 1993: 91: 961-968), which is a B cell line that is made by infecting human B cells with Epstein-Barr virus in a test tube. The EBV-LCL cells may be directly prepared and used in a general laboratory by a method of adding cyclosporine A in a process of infecting EBV in the PBMC. In some embodiments, the EBV-LCL cell may be prepared by following steps. $30 \times 10^6$ PBMCs are added in 9 ml, of a culture medium, the mixture is added in a T 25 culture flask, and then 9 mL of an EBV supernatant is added. 80 µL of cyclosporine A (50 µg/mL) is added and then cultured at 37° C. After 7 days of culture, a half of supernatant is removed, a fresh culture medium is added, and then 40 µL of cyclosporine A is added. The same process may be repeated once every 7 days until 28 days of culture. The cell line may be usable after 28 days of culture, and from this time, the cell line may be cultured in the culture medium without adding cyclosporine A.

The Jurkat cells and the EBV-LCL cells may be used as the feeder cells after irradiation.

In some embodiments, the irradiated Jurkat cells and the irradiated EBV-LCL cells may be included at a content ratio of 1:0.1-5, 1:0.1-4, 1:0.1-3, 1:0.1-2, 1:0.1-1.5, 1:0.5-1.5, 1:0.75-1.25, 0.1-5:1, 0.1-4:1, 0.1-3:1, 0.1-2:1, 0.1-1.5:1, 0.5-1.5:1 or 0.75-1.25:1. For example, the irradiated Jurkat cells and the irradiated EBV-LCL cells may be included at a content ratio of 1:1.

In some embodiments, the irradiated Jurkat cells and the irradiated EBV-LCL cells may be obtained by treating with irradiation of 50-500, 50-400, 50-300, 50-200, 50-150, 70-130, 80-120 or 90-110 Gy. For example, the irradiated Jurkat cells and/or the irradiated EBV-LCL cells may be obtained by treating Jurkat cells and/or EBV-LCL cells with irradiation of 100 Gy.

In some embodiments, the culturing may be performed for 1-50, 1-42, 1-40, 1-35, 1-20, 1-19, 1-18, 1-17, 1-16, 1-15 or 1-14 days.

In some embodiments, the culturing step may further include following steps: co-culturing with the feeder cells and a first cytokine ("first culturing step"); and further co-culturing after addition of a second cytokine ("second culturing step")

The second culturing step may include adding the second cytokine once or more between day 0-6 of culturing. For example, the second culturing step may include adding the second cytokine once on each of day 0 and day 3 of culturing.

The second culturing step may include adding the second cytokine and the feeder cells during the first 6 days of the cycle of 14 days of culturing. For example, the second culturing step may include adding the feeder cells during a 14 days cycle, and adding the second cytokine on day 3 and 6 of each cycle once each.

In some embodiments, the first cytokine may be IL-2. In some embodiments, the second cytokine may be IL-21. In some embodiments, the second cytokine may be used at the concentration of 10-1000, 10-500, 10-100, 20-100, 30-100, 40-100, 50-100 of 10-50 ng/mL. In some embodiments, culturing with the addition of the second cytokine once or more during day 0-6 may exhibit superior proliferation and/or anti-cancer activity. In some embodiments, culturing with the addition of the feeder cells and the second cytokine for six days in the cycle of 14 days may exhibit superior proliferation and/or anti-cancer activity.

In some embodiments, the co-culturing may be performed by including the peripheral blood mononuclear cells and the feeder cells (for example, the Jurkat cells and the EBV-LCL cells) at a mixing ratio of 1:1-100, 1:1-90, 1:1-80, 1:1-70, 1:10-65, 1:20-65, 1:30-65, 1:40-65, 1:50-65 or 1:55-65.

The co-culturing may be performed in a medium and any suitable media generally used for induction and proliferation of the peripheral blood mononuclear cells to the NK cells in the art may be used without a limitation as such a medium. For example, an RPMI-1640, DMEM, x-vivo10, x-vivo20, or cellgro SCGM medium may be used as such a medium. In addition, the culture conditions such as a temperature may follow any suitable culture conditions of the peripheral blood mononuclear cells known in the art.

In some embodiments, within the produced NK cells, a ratio or purity of the CD56+ NK cells may be 85% or more, 90% or more, or 95% or more, or 98% or more with respect to the whole cells. In some embodiments, within the produced NK cells, a ratio of T cells to whole cells may be 15% or less, 10% or less, 5% or less, 2% or less, 1% or less.

Cell Therapeutic Composition for Treating Cancer

According to some embodiments, a cell therapeutic composition for the treatment of cancer may include peripheral blood derived CD56+ NK cells and a cytokine.

In the present specification, the term "peripheral blood-derived" may mean that the cells are derived from "whole blood of the peripheral blood" or "leukocytes isolated from the peripheral blood using leukapheresis." The peripheral blood derived CD56+ NK cells may be used interchangeably with peripheral blood mononuclear cell (PBMC) derived CD56+ NK cells.

In some embodiments, the cytokine may be used at a concentration of 18-180,000, 20-100,000, 50-50,000, 50-1, 000, 50-900, 50-800, 50-700, 50-600, 50-550, 100-550, 150-550, 200-550, 250-550, 300-550, 350-550, 400-550, 450-550 IU/mL When the cytokine is used in these ranges, it may suppress apoptosis of the NK cells included in the cancer treatment composition, and increase anti-cancer activity of the NK cells.

In some embodiments, the composition may include IL-2 as the cytokine.

In some embodiments, the CD56+ NK cells may be obtained as described elsewhere herein. For example, the CD56+ NK cells may be obtained by coculturing with feeder cells (e.g. irradiated Jurkat cells and irradiated EBV-LCL cells). In some embodiments, the ratio of CD56+ NK cells to whole cells (purity) may be 85% or more, 90% or more, 95% or more, or 98% or more.

In some embodiments, the cancer may be blood cancer, stomach cancer, pancreatic cancer, cholangiocarcinoma, colon cancer, breast cancer, liver cancer, ovarian cancer, lung cancer, kidney cancer, prostate cancer or neuroblastoma, but not limited thereto.

In some embodiments, the composition may not include T cells, or may include only trace amount of T cells. For example, the ratio of T cells to whole cells in the composition may be less than 15%, less than 10%, less than 5%, less than 2%, less than 1% or less.

In the present specification, the term "T cell" refers to a lymphocyte derived from thymus, which can "memorize" previously encountered antigens and provide information to B cells, thereby facilitates production of antibody and plays an important role in cell immune system. Since these T cells may distinguish very small differences among different antigens to induce an immune response to allogenic antigens, autologous therapy is possible, but there may be a limit to be used for allogenic therapy. Accordingly, the cell therapeutic composition without T cells may be suitable for allotransplantation.

In the present specification, the term "cell therapeutic agent" refers to a medicine which is used for treatment, diagnosis, and prevention through a series of actions, such as proliferating and screening autologous, allogenic, and xenogenic living cells in vitro for restoring functions of cells and tissues or changing biological characteristics of the cells by other methods. The cell therapeutic agents have been regulated as medical products from 1993 in USA and 2002 in Korea. These cell therapeutic agents may be largely classified into two fields, that are, first, stem cell therapeutic agents for tissue regeneration or recovery of organ functions, and second, immune cell therapeutic agents for regulation of immune responses, such as inhibition of the immune response or enhancement of the immune response in vivo.

An administration route of cell therapeutic compositions described herein may be any suitable route as long as the composition reaches a target tissue. The administration may be parenteral administration, for example, intraperitoneal administration, intravenous administration, intramuscular administration, subcutaneous administration, or intradermal administration, but not limited thereto.

The cell therapeutic composition described herein may be formulated in a suitable form together with a pharmaceutically acceptable carrier suitable or generally used for cell therapy. The "pharmaceutically acceptable" refers to a composition which is physiologically acceptable and does not generally cause an allergic reaction such as gastrointestinal disorders, dizziness, or the like, or similar reactions thereto, when being administered to the human body. The pharmaceutically acceptable carrier may include, for example, parenteral administration carries such as water, suitable oils, saline, aqueous glucose and glycol, and the like, and further include stabilizers and preservatives. The suitable stabilizer includes an antioxidant such as sodium hydrogen sulfite, sodium sulfite, or ascorbic acid, sucrose, albumin, or the like. The suitable preservative includes DMSO, glycerol, ethylene glycol, sucrose, trehalose, dextrose, polyvinylpyrrolidone, or the like.

The cell therapeutic composition may also be administered by any device in which the cell therapeutic agent may move to the target cell.

The cell therapeutic composition may include a therapeutically effective amount of cell therapeutic agent for treatment of diseases. The term "therapeutically effective amount" means an amount of an active ingredient or a cell therapeutic composition which induces biological or medical responses in tissue systems, animals, or humans which are considered by researchers, veterinarians, physicians, or other clinicians, and includes an amount of inducing alleviation of symptoms of diseases or disorders to be treated. It will be apparent to those skilled in the art that the cell therapeutic agent included in the cell therapeutic composition may be changed according to a desired effect. Therefore, the optimal content of the cell therapeutic agent may be easily determined by those skilled in the art, and may be adjusted according to various factors including a type of disease, severity of the disease, contents of other ingredients contained in the composition, a type of formulation, and an age, a weight, a general health condition, a gender, and a diet of a patient, an administration time, an administration route, a secretion ratio of the composition, a treatment period, and simultaneously used drugs. It is important to include an amount capable of obtaining a maximum effect by a minimum amount without side effects by considering all of the factors. For example, the cell therapeutic composition may include a cell therapeutic agent of $1 \times 10^6$ to $5 \times 10^8$ cells per kg of body weight.

Method for Preventing or Treating Cancer

Further, according to another aspect of the invention, a method for preventing or treating cancer is provided, the method comprising administering a cell therapeutic composition for anti-cancer including peripheral blood-derived CD56+ natural killer cells and cytokines to a subject. The term "subject" refers to a mammal which is a subject for treatment, observation, or testing, and preferably, a human. The subject may be a patient of blood cancer, stomach cancer, pancreatic cancer, cholangiocarcinoma, colon cancer, breast cancer, liver cancer, ovarian cancer, lung cancer, kidney cancer, prostate cancer or neuroblastoma, but not limited thereto.

In some embodiments, in the case of an adult, the cell therapeutic composition may be administered once to several times a day. The cell therapeutic composition may be administered every day or in a 2-180 day interval the cell therapeutic agent included in the composition may include $1 \times 10^6$ to $1 \times 10^{11}$ peripheral blood-derived CD56+ natural killer cells, for example, about $1 \times 10^6$ to $1 \times 10^8$ NK cells per kg of body weight. In some embodiments, the peripheral blood-derived CD56+ natural killer cells in the cell therapeutic composition are at least about 90% pure. In some embodiments, the cytokine is IL-2 at a concentration ranging from about 50-50,000 IU/ml.

In some embodiments, the cell therapeutic composition of the present invention may be administered by any suitable method, such as administration through a rectal, intravenous, intraarterial, intraperitoneal, intramuscular, intrasternal, percutaneous, topical, intraocular, or intradermal route. In some embodiments, the NK cells included in the composition may be allogenic, i.e. obtained from a person other than the subject being treated. In some embodiments, the person may be a normal person or a cancer patient. In some embodiments, the NK cells included in the composition may be autologous, i.e. obtained from the subject being treated.

In some embodiments, the NK cells disclosed herein and the cell therapeutic composition including the NK cells disclosed herein may be used for treating disease or condition other than cancer. It has been reported that NK cells plays an important role in the regulation of immune system, for example, by regulating of T-cells, thus the cell therapeutic composition having the NK cells may be administered to treat conditions associated with the immune system. For example, the cell therapeutic composition may be administered to treat neurodegenerative disorders (e.g. Alzheimer's disease and Parkinson's disease) or autoimmune diseases (e.g. rheumatoid arthritis, multiple sclerosis, psoriasis, spondyloarthropathies, SLE, Sjogren's syndrome, systemic sclerosis).

Advantageous Effects

Features and advantages of the present invention are summarized as follows:

(a) The present invention, relates to a method of producing natural killer cells.

(b) According to the method of producing natural killer cells, since the high-purity natural killer cells in which the T cells and the like are removed can be produced without using various expensive cytokines, it is possible to enhance an effect of prevention and treatment of cancer, particularly, allogenic therapy using the natural killer cells.

(c) The present invention relates to a cell therapeutic composition for anti-cancer comprising peripheral blood-derived CD56+ NK cells and cytokines.

(d) The composition of the present invention includes high-purity natural killer cells with minimal (e.g., less than about 1%) T cells, and thus the composition may be effectively used for allogenic therapy as well as autologous therapy.

EXAMPLES

The following examples are provided to illustrate certain particular features and/or embodiments. These examples should not be construed to limit the disclosure to the particular features or embodiments described.

Example 1. Production of CD56+ Natural Killer (NK) Cells

CD56+ cells and CD3−/CD56+ cells were isolated from PBMCs by the following method. First, the PBMCs were isolated from the blood using a Ficoll-Hypaque density gradient method and then the cells were counted.

Example 1-1. Preparation, for Producing CD56+ Cells

The counted PBMCs were added with a MACS buffer (1×PBS+0.5% HSA) and suspended, and added with CD56 microbeads (Miltenyi Biotec) to be 1 to 20 µL per $1.0×10^7$ PBMCs, and then incubated at 2 to 8° C. for 5 to 30 minutes. After incubation, the MACS buffer was added and mixed, and then the mixture was centrifuged (600×g) to precipitate the cells. After centrifugation, a supernatant was removed, and the cells were suspended by adding the MACS buffer and added in a column connected to a MACS separator. The MACS buffer passed through the column to remove non-specific binding. The column was separated from the MACS separator and transferred to a 15 mL conical tube, and then added with the MACS buffer to isolate CD56+ cells attached to the column.

Example 1-2. Preparation for Producing CD3−/CD56+ Cells

The counted PBMCs were added with a MACS buffer (1×PBS±0.5% HSA) and suspended, and added with CD3 microbeads (Miltenyi Biotec) to be 1 to 20 µL per $1.0×10^7$ PBMCs, and then incubated at 2 to 8° C. for 5 to 30 minutes. Alter incubation, the MACS buffer was added and mixed, and then the mixture was centrifuged (600×g) to precipitate the cells. After centrifugation, a supernatant was removed, and the cells were suspended by adding the MACS buffer and added in a column connected to a MACS separator. The MACS buffer passed through the column to collect CD3− cells. The collected CD3− cells were added with a MACS buffer (1×PBS+0.5% HSA) and suspended, and added with CD56 microbeads (Miltenyi Biotec) to be 1 to 20 µL per $1.0×10^7$ CD3− cells, and then incubated at 2 to 8° C. for 5 to 30 minutes. After incubation, the MACS buffer was added and mixed, and then the mixture was centrifuged (600×g) to precipitate the cells. After centrifugation, a supernatant was removed, and the cells were suspended by adding the MACS buffer and added in a column connected to a MACS separator. The MACS buffer passed through the column to remove non-specific binding. The column was separated from the MACS separator and transferred to a 15 mL conical tube, and then added with the MACS buffer to isolate CD3−/CD56+ cells attached to the column.

Example 1-3. Production of NK Cells Using the CD56+ Cells and CD3−/CD56+ Cells The CD56+ cells or the CD3−/CD56+ cells isolated from the PBMCS as in Examples 1-1 and 1-2 were added in a RPMI-1640 medium containing PBS 10% added with IL-2 at a concentration of 500 IU/mL together with prepared combination of feeder cells (Jurkat cells and EBV-LCL cells) irradiated with 100 Gy radiation and then co-cultured in an incubator at 37° C. and 5% $CO_2$. The ratio of (CD56+ cells and/or CD3−/CD56+ cells):(Jurkat cells):(OBV-LCL cells) was about 1:30:30.

Meanwhile, the Jurkat cells may be obtained from ATCC (ATCC TIB-152), and the EBV-LCL cells were prepared by the following method: $30×10^6$ PBMCs were added in 9 mL of a culture medium, the mixture was added in a T 25 culture flask, and then 9 m of an EBV supernatant was added. 80 µL of cyclosporine A was added and then cultured at 37° C. After 7 days of culture, a half of supernatant was removed, a fresh culture medium was added, and then 40 µL of cyclosporine A was added. The same process as the 7th day was repeated once every 7 days until 28 days of culture. The cell line was usable after 28 days of culture, and from this time, the cell line was cultured in the culture medium without adding cyclosporine A.

Example 2. Production of CD56+ Natural Killer (NK) Cells (IL-2/IL-21 Treated)

NK cells were produced using same method of Example 1 (1-1 to 1-3), except for adding IL-2 (500 IU/mL) and IL-21 (50 ng/mL) instead of IL-2 (500 IU/mL).

Comparative Example 1. Production of Natural Killer (NK) Cells Without the CP56+ Cells Isolation Step (IL-2 Treated)

PBMCs were isolated from the blood using a Ficoll-Hypaque density gradient method. The PBMCs were added in a RPMI-1640 medium containing FBS 10% added with IL-2 at a concentration of 500 IU/mL together with prepared feeder cells (Jurkat cells and EBV-LCL cells) irradiated with 100 Gy radiation and then co-cultured in an incubator at 37° C. and 5% $CO_2$.

Comparative Example 2. Production of Natural Killer (NK) Cells Without the CP56+ Cells Isolation Step (IL-2/IL-21 Treated)

NK cells were produced using same method of Comparative Example 1, except for adding IL-2 (500 IU/mL) and IL-21 (50 ng/mL) instead of IL-2 (500 IU/mL).

Comparative Examples 3&4. Production of Natural Killer (NK) Cells Without the CP56+ Cells Isolation Step NK cells were produced using similar methods of Comparative Examples 1&2, respectively, except for that a ratio of PBMC:(Jurkat cells):(EBV-LCL cells) was 1:0.5:0.5.

Experimental Example 1. Continuation of Proliferation Ability of NK Cells

With respect to each of the NK cells cultured in a $CO_2$ incubator according to Examples 1, 2 and Comparative Examples 1, 2, on Day 6 of culture in a T 25 culture flask, cells were inoculated into a 350 mL bag on the basis of the cell number of $1.0×10^6$ to $2.0×10^6$/mL and further cultured for 4 days. On Day 10 of culture, the cells were inoculated into a 1 L bag on the basis of the cell number of $1.0×10^5$ to $2.0×10^6$/mL and then further cultured for 4 days. Finally, on Day 14 of culture, the cells were inoculated into a 1 L bag on the basis of the cell number of $1.0×10^5$ to $2.0×10^6$/mL and then further cultured for 3 to 6 days.

FIG. 1A illustrates the fold increase of NK cells during the culture. As illustrated in FIG. 1A and Table 1 below, the CD56+ NK cells (CD56+ and CD3−/CD56+) of Example 1 were proliferated 2675 and 1903 times respectively on Day 17 compared to Day 0, while the PBMC cells of Comparative Example 1 was proliferated 1768 times on Day 17 compared to Day 0.

TABLE 1

| | Expansion Folds | | | | |
|---|---|---|---|---|---|
| | DAY 0 | DAY 6 | DAY 10 | DAY 14 | DAY 17 |
| PBMC | 1 | 2 | 52 | 608 | 1768 |
| CD56+ | 1 | 8 | 188 | 1311 | 2675 |
| CD3−/CD56+ | 1 | 6 | 142 | 966 | 1903 |

Figure 1B:
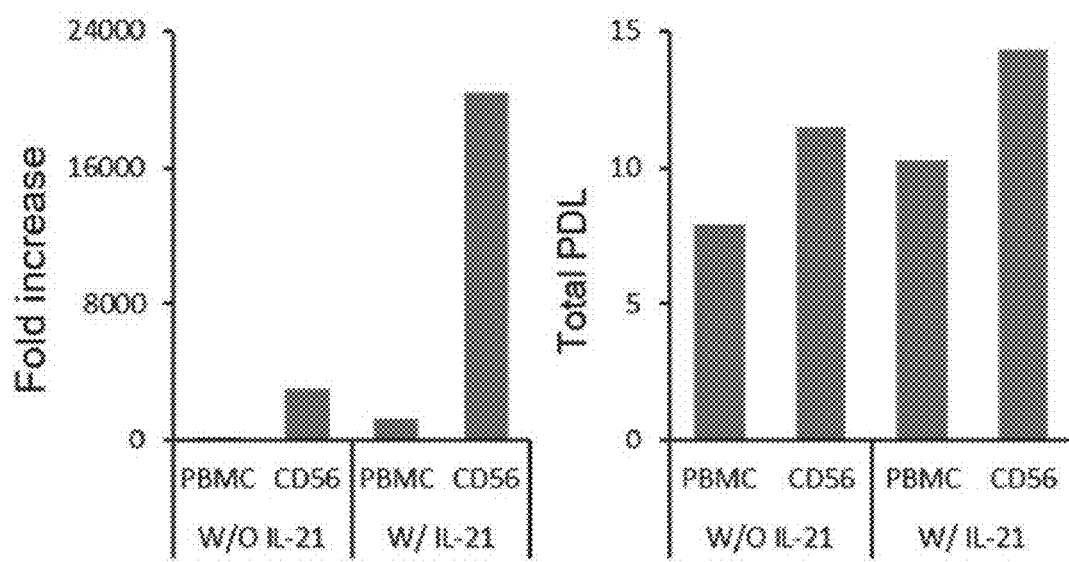
FIG. 1B illustrates graphs showing cell growth rates of NK cells produced from PBMCs and CD56+ cells with or without treating with IL-21.

FIG. 1B illustrates the fold increase and the papulation doubling level (PDL) of NK cells. Further, as illustrated in FIG. 1B, the PBMCs of Comparative Example 1 (PBMC w/o IL-21) and Comparative Example 2 (PBMC w/IL-21) were proliferated 243 and 1248 times respectively compared to Day 0, while the CD56+ NK cells of Example 1 (CD56 w/o IL-21) and Example 2 (CD56 w/IL-21) were proliferated 2990 and 20434 times respectively compared to Day 0.

Experimental Example 2. Confirmation of Purity of CD56+ NK Cells

The NK cells of Examples 1, 2 and Comparative Examples 1, 2 were washed once with a FACS staining buffer and suspended in 100 μL, and then stored at 2 to 8° C. for 20 to 30 minutes under a dark condition after mixing with a monoclonal antibody binding with fluorescence. After one additional washing, the cells were suspended in 300 to 500 μL of the FACS staining buffer and then 10,000 to 100,000 cells per tube were obtained and analyzed by using a CD56-FITC/CD3-PE/CD20-PerCP5/CD14-APC panel of a flow cytometer. The purify of the CD56+ NK cells was defined as a ratio of cells introduced in a CD3−/CD56+ region after FSC/SSC gating, and it was further confirmed that CD20 and CD14 were not expressed in the cells in the CD3−/CD56+ region.

Figure 2:
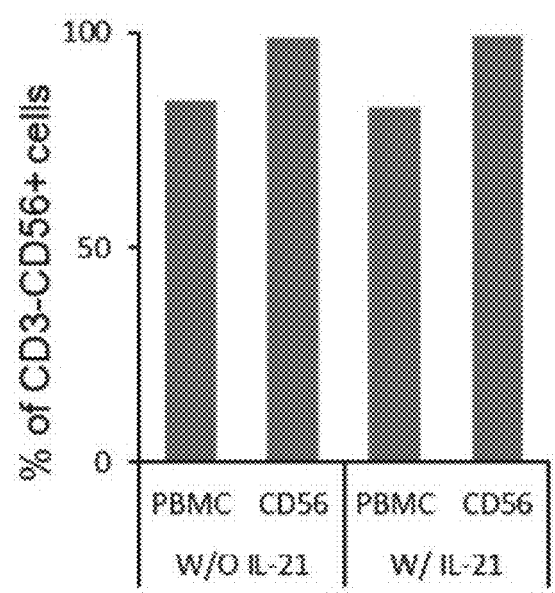
FIG. 2 illustrates a graph showing the purity of CD3−/CD56+ NK cells produced from PBMCs or CD564 cells with or without treating with IL-21.

As illustrated in FIG. 2, the purity of NK cells of Comparative Example 1 (PBMCs w/o IL-21) and Comparative Example 2 (PBMCs w/IL-21) were 84.2% and 84.7% respectively, while the purity of NK cells of Example 1 (CD56 w/o IL-21) and Example 2 (CD56 w/IL-21) were 98.6% and 99.2% respectively.

Experimental Example 3. Continuation of Cancer Cell Cytotoxicity of NK Cells

First, the cytotoxicity against K562 cells (blood cancer, ATCC® CCL-243™), a chronic myelogenous leukemia cell line was confirmed.

Before used in the experiment, K562 cells were prepared by subculturing K562 cells suspended in a RPMI 1640 medium containing FBS 10%, at 37±1° C. at an interval of three days, for 7 days or more.

The prepared K562 cells were suspended in the RPMI-1640 medium at a concentration of $1.0\times10^6$ cells/mL, and added with a fluorescent material (Calcein-AM) at a concentration of 4 μM. The K562 cells were stained at 37±1° C. for 30 minutes, and then inverted at an interval of ten minutes. The K562 cells stained with the fluorescent material were centrifuged at 3,300 rpm for 3 minutes, washed three times, and then suspended in an SNK medium containing FBS 10%, at a ratio of $1.0\times10^6$ cells/mL. The K562 cells were inoculated into a round bottom microwell plate (96-well) in an amount of $1.0\times10^4$ cells per well.

The NK cells of the Experimental Example 1 (effector cells) on the 14 to 20th days of culture were suspended and diluted in a RPMI-1640 medium containing FBS 10% at ratios of $1.0\times10^6$ cells/mL, $3.0\times10^5$ cells/mL, $1.0\times10^5$ cells/mL and $0.5\times10^5$ cells/mL, respectively.

The diluted effector cells were inoculated into the plate inoculated with the target cells (the K562 cells) at a concentration of 100 μL per well for three wells each (triplication), respectively, in this case, ratios of the effector cells and the target cells are shown in Table 2 below.

TABLE 2

| Effector:Target | Effector cells | Target cells |
|---|---|---|
| 10:1 | $1.0 \times 10^3$ | $1.0 \times 10^4$ |
| 3:1 | $3.0 \times 10^4$ | $1.0 \times 10^4$ |
| 1:1 | $1.0 \times 10^4$ | $1.0 \times 10^4$ |
| 0.5:1 | $0.5 \times 10^4$ | $1.0 \times 10^4$ |

Figure 3:
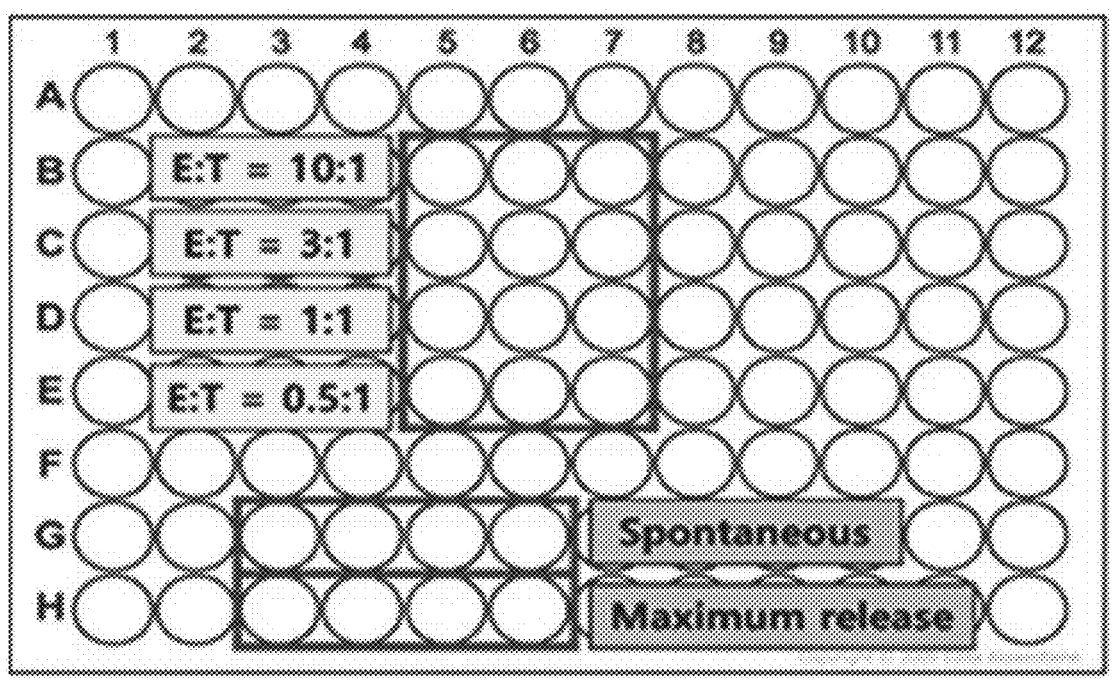
FIG. 3 illustrates a plate design for analyzing anticancer activity of NK cells.

The plate design used in the present experiment is shown in FIG. 3, in a negative control group (Spontaneous), fluorescence-stained living K562 cells were added, and in a positive control group (Maximum release), the K562 cells were completely killed using TX-100 and exhibited a maximum fluorescence.

The plate inoculated with the target cells and the effector cells was centrifuged at 1000 rpm for 5 minutes, cultured at 37±1° C. for 3 to 4 hours, and then centrifuged again at 1000 rpm for 5 minutes. After centrifugation, 80 μL of a supernatant was transferred to a black plate (96-well), and then a fluorescence amount was measured using a fluorescence microplate reader and the cytotoxicity against cancer cells was calculated using Equation 1 below.

$$\text{Cytotoxicity} = \frac{\text{Test Release} - \text{Spontaneous Release}}{\text{Maximum Release} - \text{Spontaneous Release}} \times 100 \quad \text{Equation 1}$$

Figure 4A:
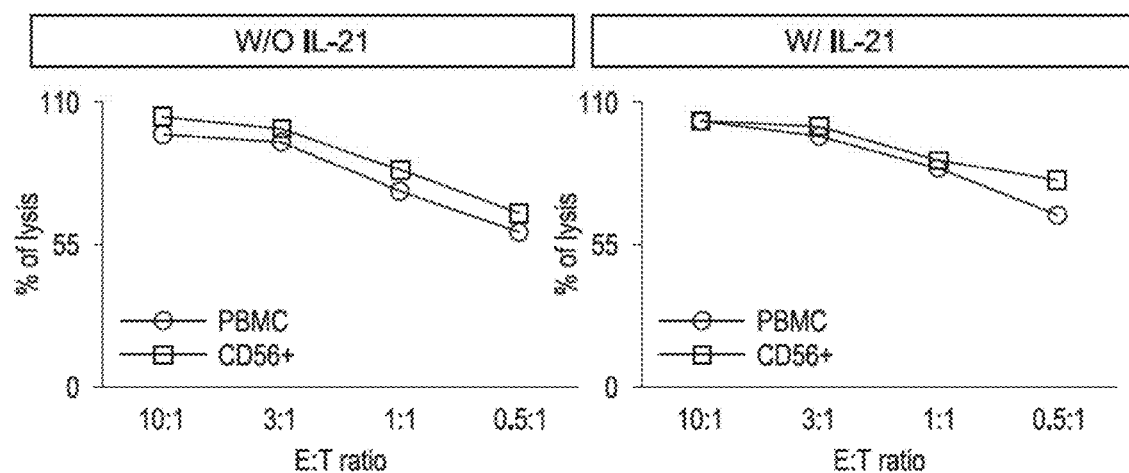
FIG. 4A illustrates graphs showing the short-term cytotoxicity of NK cells produced from PBMCs and CD56+ cells for various effector cell:target cell (E:T) ratios.

FIG. 4A and Table 3 below show % of lysis of K562 cells at various E:T ratio. As illustrated in FIG. 4A and Table 3 below, as compared with Comparative Example 3 (PBMCs w/o IL-21) and Comparative Example 4 (PBMCs w/IL-21), the CD56+ cells cultured according to Example 1 (CD56+ w/o IL-21) and Example 2 (CD56+ w/IL-21) exhibited higher anti-cancer activity.

TABLE 3

| | % of lysis | | | |
|---|---|---|---|---|
| | E:T (10:1) | E:T (3:1) | E:T (1:1) | E:T (0.5:1) |
| PBMC(W/O IL-21) | 97.5 | 94.6 | 75.3 | 60.0 |
| PBMC(W/ IL-21) | 102.3 | 97.1 | 84.8 | 66.9 |
| CD56(W/O IL-21) | 103.3 | 99.9 | 83.8 | 67.4 |
| CD56+(W/ IL-21) | 102.9 | 100.7 | 87.7 | 80.0 |

Next, the cytotoxicity against solid tumor cells, which are known to have greater tolerance against NK cells, is confirmed. AGS (stomach cancer, ATCC® CRL-1739™). A549

(king cancer. ATCC® CRL-185™), and MDA-MB0231 (breast cancer, ATCC® HTB-26™) were used as solid tumor cell lines.

Each solid tumor cells were tagged with green-fluorescent marker using CYTO-ID® Green long-term tracer kit (Enzo Life Sciences Inc.) inoculated on a plate, and cultured for 24 hours. Next day, NK cells and cancer cells were reacted for 48 hours in 0.5:1 ratio. After 48 hours, cytotoxicity was confirmed by measuring the number of cells exhibiting green-fluorescence using flow cytometer.

Figure 4B:
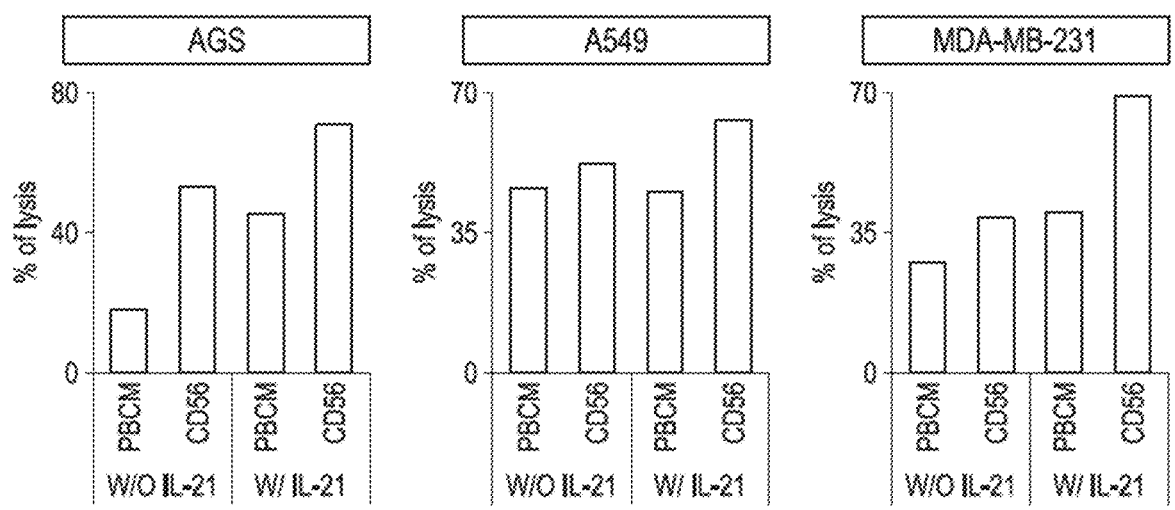
FIG. 4B illustrates graphs showing the long-term cytotoxicity of NK cells produced from PBMCs and CD56+ cells against AGS, A549, and MDA-MB-231 cells.

As illustrated in FIG. 4B, as compared with Comparative Example 1 (PBMCs w/o IL-21) and Comparative Example 2 (PBMCs w/IL-21), the CD56+ cells cultured according to Example 1 (CD56+ w/o IL-21) and Example 2 (CD56+ w/IL-21) exhibited higher anti-cancer activity.

Experimental Example 4. Comparison of Proliferative Ability of NK Cells Depending on Timing and Number of IL-21 Treatment To evaluate the proliferative ability of NK cells according to the timing of IL-21 treatment, experiments as outlined below were conducted.

CD56+ NK cells were produced according to the method of Example 1, but treated with IL-21 (50 ng/mL) during Day 0-6 (D0-6 group). Day 6-10 (D6-10 group), Day 10-14 (D10-14 group). Of Day 14-17 (D-14-17 group), and the proliferative ability of the CD56+ NK cells were compared using the method according to Experimental Example 1.

NK cells were treated with IL-21: for the D0-6 group, twice, on Day 0 and 3; for the D6-10 group, once, on Day 6; for the D10-14 group, once, on Day 10: for the D14-17 group, once, on Day 14. For a control group, NK cells were not treated with IL-21.

Figure 5A:
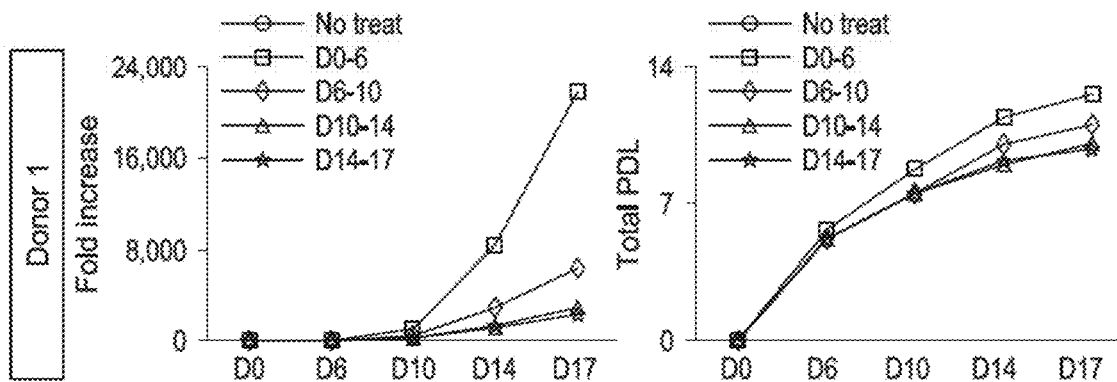
FIGS. 5A-5B illustrate graphs showing cell growth rales of NK cells produced by treating with IL-21 during various periods.

As shown in FIG. 5A and Table 4, the D10-14 group and the D14-17 group did not exhibit significant difference in proliferative ability as compared with the control group, while the D0-6 group and the D6-10 group exhibited increased proliferation ability as compared with the control group. Especially, the D0-6 group exhibited the greatest expansion fold increase.

TABLE 4

| | Expansion Folds | | | |
|---|---|---|---|---|
| control | D0-6 | D6-10 | D10-14 | D14-17 |
| Donor 1   2996 | 21859 | 6388 | 2894 | 2330 |

To evaluate the proliferative ability of NK cells according to the number of IL-21 treatments, experiments as outlined below were conducted.

CD56+ NK cells were produced according to the method of Example 1, but treated with IL-21 (50 ng/mL) during Day 0-3 (D0-3 group). Day 3-6 (D3-6 group), or Day 0-6 (D0-6 group), and the proliferative ability of the CD56+ NK cells were compared using the method according to Experimental Example 1.

NK cells were treated with IL-21: for the D0-3 group, once, on Day 0; for the D3-6 group, once, on Day 3; for the D0-6 group, twice, on Day 0 and 3. For a control group, NK cells were not treated with IL-21.

Figure 5B:
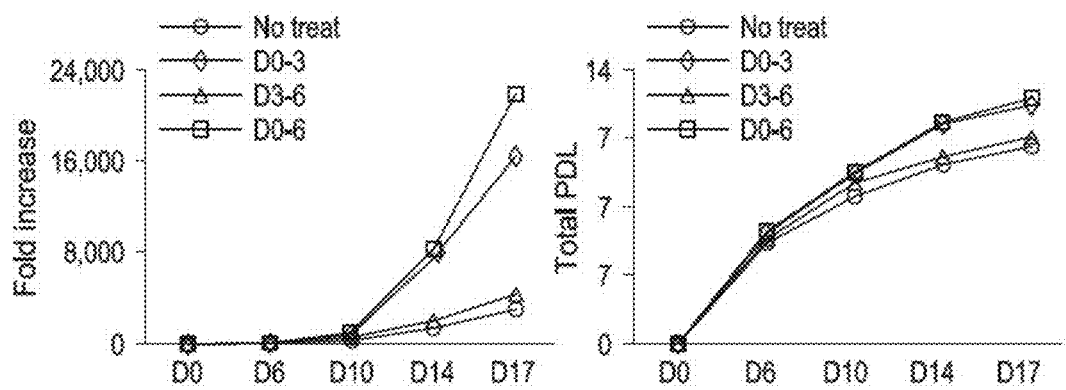

As shown in FIG. 5B and Table 5, every group with 11-21 treatment during earlier stage of the culture exhibited increased expansion fold as compared with the control group. Especially, D0-6 exhibited the greatest expansion fold increase.

TABLE 5

| | Expansion Fold | | | |
|---|---|---|---|---|
| | control | D0-3 | D3-6 | D0-6 |
| Donor 1 | 2996 | 16420 | 4360 | 21859 |

Experimental Example 5. Comparison of Proliferative Ability of NK Cells Depending on the Concentration of IL-21 Treatment CD56+ NK cells were produced according to the method of Example 1, but treated with IL-21 with a concentration of 0 ng/mL, 10 ng/mL, 30 ng/mL, 50 ng/mL or 100 ng/mL twice, and the proliferative ability of the CD56+ NK cells were compared using the method according to Experimental Example 1.

Figure 6:
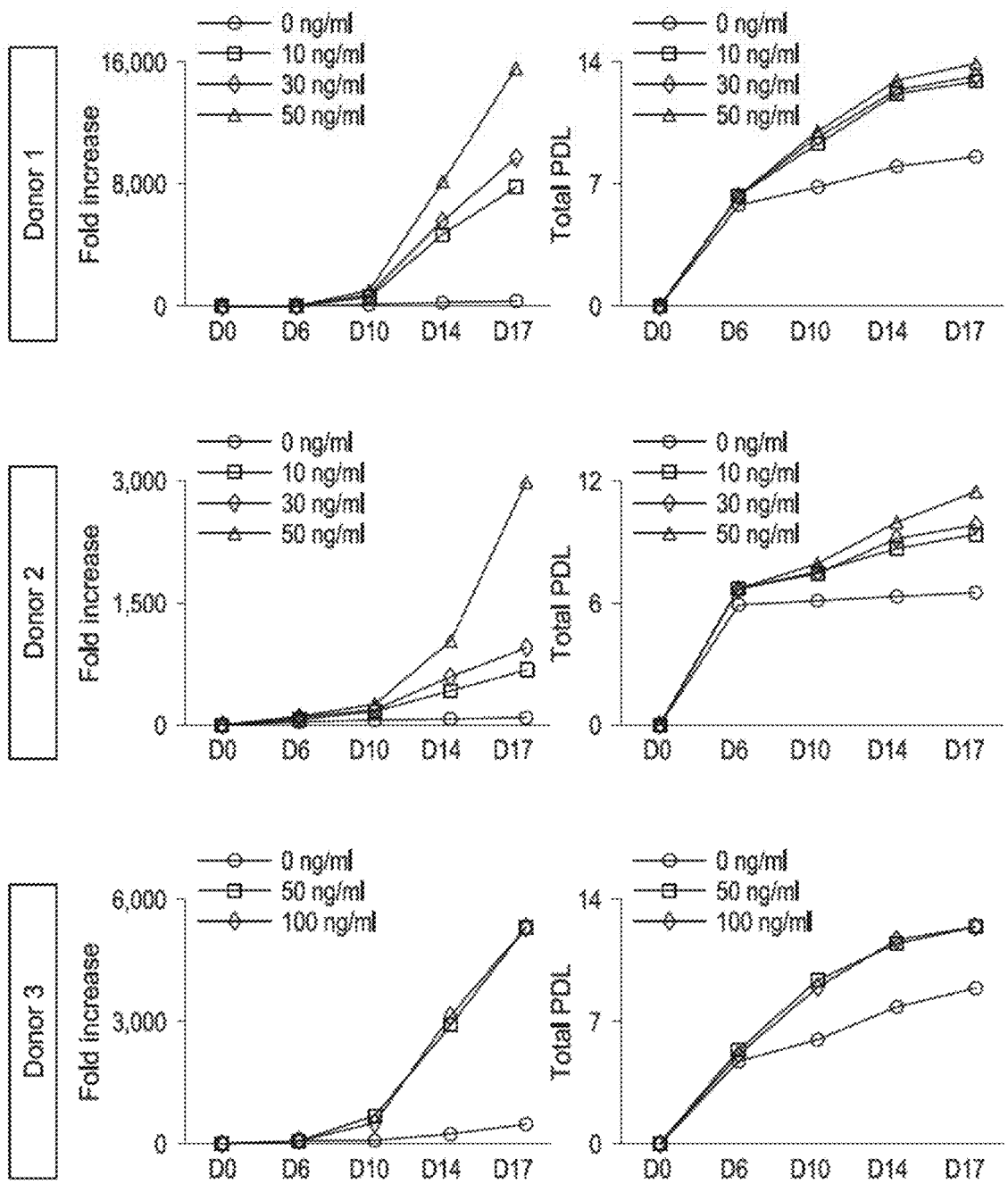
FIG. 6 illustrates graphs showing cell growth rates of NK cells produced by treating with IL-21 with various concentrations.

As shown in FIG. 6, even when treated with IL-21 with a concentration of 10 ng/mL, the NK cells exhibited greater expansion fold as compared with the NK cells with no IL-21 treatment, and the expansion told of the NK cells increased as the concentration of IL-21 increases between 10 ng/mL-50 ng/mL. However, when treated with IL-21 with a concentration of 100 ng/mL, the NK cells did not exhibit significant difference in expansion from the NK cells treated with IL-21 with a concentration of 50 ng/mL.

Experimental Example 6. Comparison of Cytotoxicity of NK Cells Depending on the Timing and Number of IL-21 Treatment To evaluate the cytotoxicity of NK cells against cancer cells according to the timing of IL-21 treatment, experiments as outlined below were conducted.

CD56+ NK cells were produced according to the method of Example 1, but treated with IL-21 (50 ng/mL) during Day 0-6 (D0-6 group). Day 6-10 (D6-10 group). Day 10-14 (D10-14 group), or Day 14-17 (D-14-17 group), and the cytotoxicity of the CD56+ NK cells against blood cancer cells (K562 cells, CCL-243™) were compared using the method according to Experimental Example 3.

NK cells were treated with IL-21: for the D0-6 group, twice, on Day 0 and 3; for the D6-10 group, once, on Day 6; for the D10-14 group, once, on Day 10; for the D14-17 group, once, on Day 14. For a control group, NK cells were not treated with IL-21.

Figure 7A:
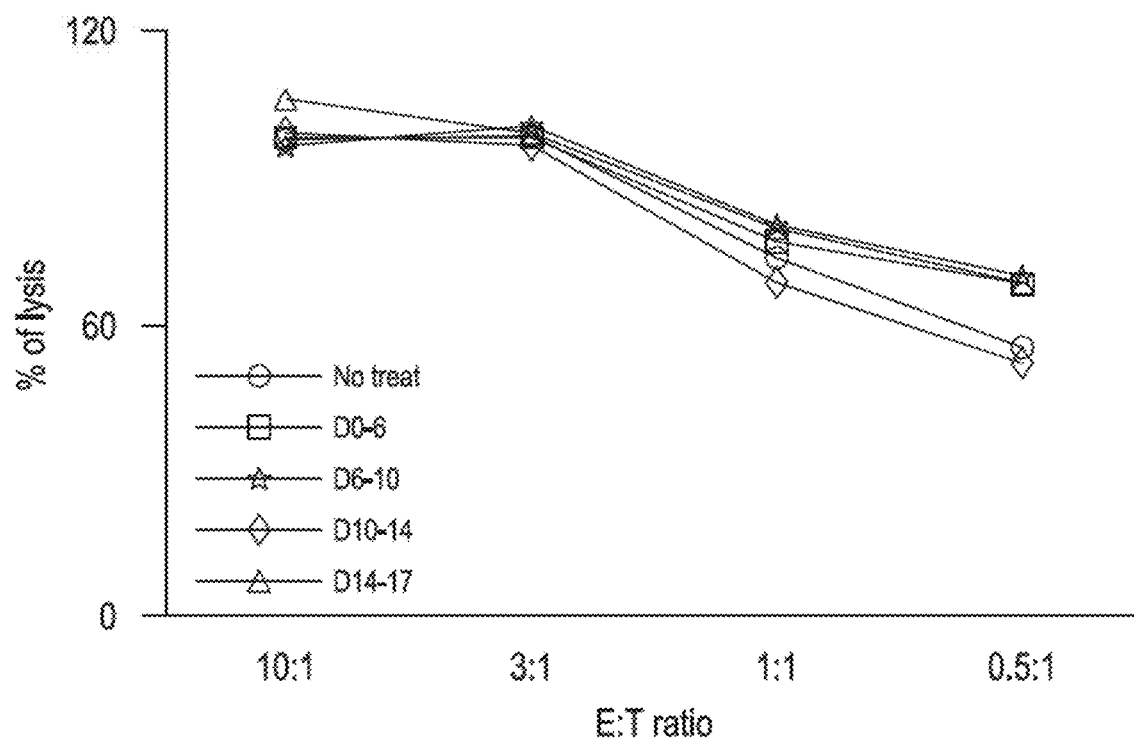
FIG. 7A illustrates a graph showing the short-term cytotoxicity of NK cells produced by treating with IL-21 during various periods for various E:T ratios.

As shown in FIG. 7A and Table 6, all groups of NK cells with IL-21 treatment, except the D14-17 group, exhibited greater anti-cancer activity as compared with the control group.

TABLE 6

| | E:T ratio | | | |
|---|---|---|---|---|
| | 10:1 | 3:1 | 1:1 | 0.5:1 |
| Control (No treat) | 98.8 | 96.9 | 73.1 | 55.1 |
| D0-6 | 98.6 | 97.0 | 77.8 | 68.4 |
| D6-10 | 96.78 | 99.1 | 80.3 | 69.8 |
| D10-14 | 98.4 | 96.6 | 68.5 | 52.4 |
| D14-17 | 104.5 | 98.8 | 79.1 | 68.8 |

Further, for each of the produced groups of CD56+ NK cells, the cytotoxicity of the CD56+ NK cells against solid tumor cells were compared using the method according to Experimental Example 3. AGS (stomach cancer, ATCC®

CRL-1739™), A549 (lung cancer, ATCC® CRL-185™), and MDA-MB0231 (breast cancer, ATCC® HTB-26™) were used as solid tumor cell lines.

Figure 7B:
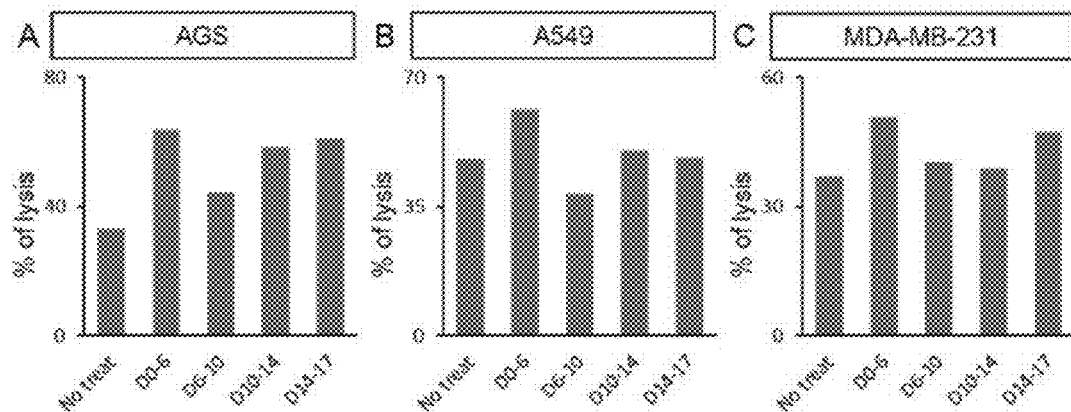
FIGS. 7B-7C illustrate long-term cytotoxicity graphs showing the long-term cytotoxicity of NK cells produced by treating with IL-21 during various periods against AGS, A549, and MDA-MB-231 cells.

As shown in FIG. 7B, the NK cells with IL-21 treatment during an earlier stage of the culture (the D0-6 group) exhibited the greatest anti-cancer activity against all three types of solid tumor cells.

To evaluate the cytotoxicity of the NK cells according to the number of IL-21 treatments, experiments as outlined below were conducted.

CD56+ NK cells were produced according to the method of Example 1, but treated with IL-21 (50 ng/mL) during Day 0-3 (D0-3 group), Day 3-6 (D3-6 group), or Day 0-6 (D0-6 group), and the cytotoxicity of the CD56+ NK cells against solid tumor cells were compared using the method according to Experimental Example 3. AGS (stomach cancer, ATCC® CRL-1739™), A549 (lung cancer, ATCC® CRL-185™), and MDA-MB0231 (breast cancer, ATCC® HTB-26™) were used as solid tumor cell lines.

NK cells were treated with TL-21: for the D0-3 group, once, on Day 0; for the D3-6 group, once, on Day 3; for the D0-6 group, twice, on Day 0 and 3. For a control group, NK cells were not treated with IL-21.

Figure 7C:
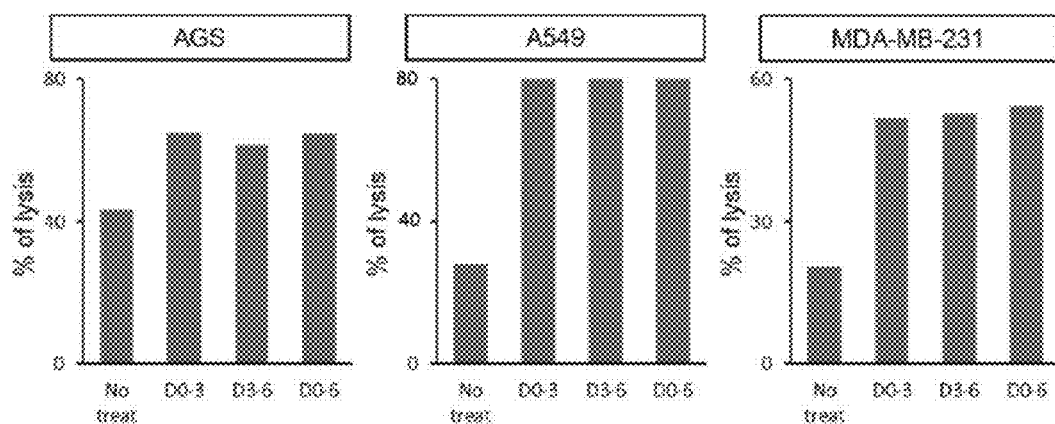

As shown in FIG. 7C, every group with IL-21 treatment during earlier stages of the culture exhibited greater anti-cancer activity as compared with the control group.

Experimental Example 7. Comparison of Cytotoxicity of NK Cells Depending on the Concentration of IL-21 Treatment CD56+ NK cells were produced according to the method of Example 1, but treated with IL-21 with a concentration of 0 ng/mL, 10 ng/mL, 30 ng/mL, 50 ng/mL or 100 ng/mL twice, and the cytotoxicity of the CD56+ NK cells against blood cancer cells (K562 cells, CCL-243™) were compared using the method according to Experimental Example 3.

As shown in FIG. 5A, most NK cells treated with IL-21 exhibited greater cytotoxicity as compared with the NK cells with no IL-21 treatment, when treated with IL-21 with a concentration of 100 ng/mL, the NK cells did not exhibit significant difference in expansion from the NK cells not treated with IL-21.

CD56+ NK cells were produced according to the method of Example 1, but treated with IL-21 with a concentration of 0 ng/mL, 10 ng/mL, 30 ng/mL, 50 ng/mL or 100 ng/mL twice, and the cytotoxicity of the CD56+ NK cells against solid tumor cells (K562 cells, CCL-243™) were compared using the method according to Experimental Example 3, AGS (stomach cancer, ATCC® CRL-1739™), A549 (lung cancer, ATCC® CRL-185™), and MDA-MB0231 (breast cancer, ATCC® HTB-26™) were used as solid tumor cell lines.

Figure 8A:
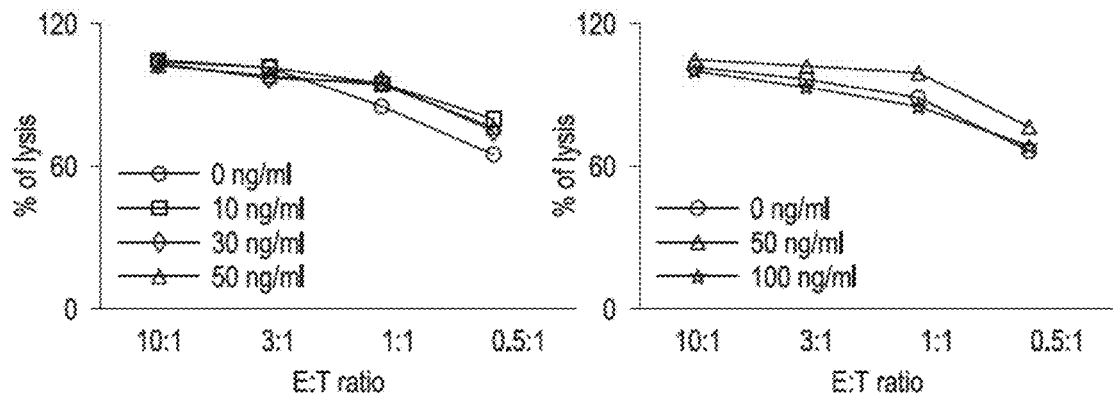
FIG. 8A illustrates graphs showing the short-term cytotoxicity of NK cells produced by treating with IL-21 with various concentrations for various E:T ratios.
Figure 8B:
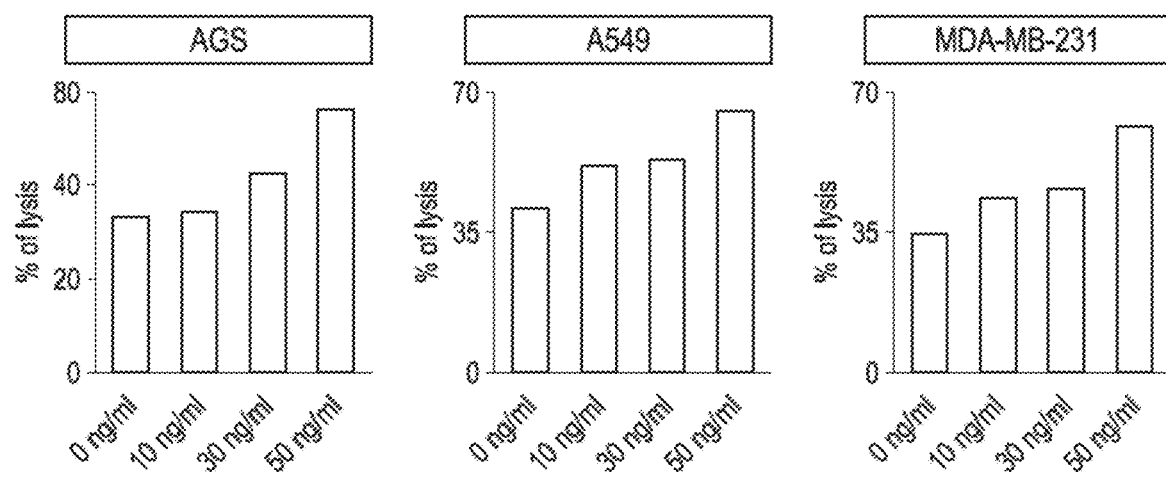
FIG. 8B illustrates graphs showing the long-term cytotoxicity of NK cells produced by treating with IL-21 with various concentrations against AGS, A549, and MDA-MB-231 cells.

As shown in FIG. 8B, the NK cells treated with IL-21 with a concentration of 50 ng/mL exhibited the greatest anti-cancer activity.

Experimental Example 8. Comparison of Proliferative Activity of NK Cells Depending on the Number of Feeder Cell Treatment To analyze whether multiple treatments with feeder cells would sustain proliferation of NK cells, the NK cells during the culture were treated with feeder cells in an interval of 14 days, and the expansion of NK cells were monitored for 42 days.

To further analyze the increase of NK cells expansion depending on IL-21 treatment, the NK cells were treated with IL-21 (50 ng/mL) twice in 3 days interval, during a six days period from each treatment with feeder cells (Day 0-6, 14-20, 28-34).

Figure 9:
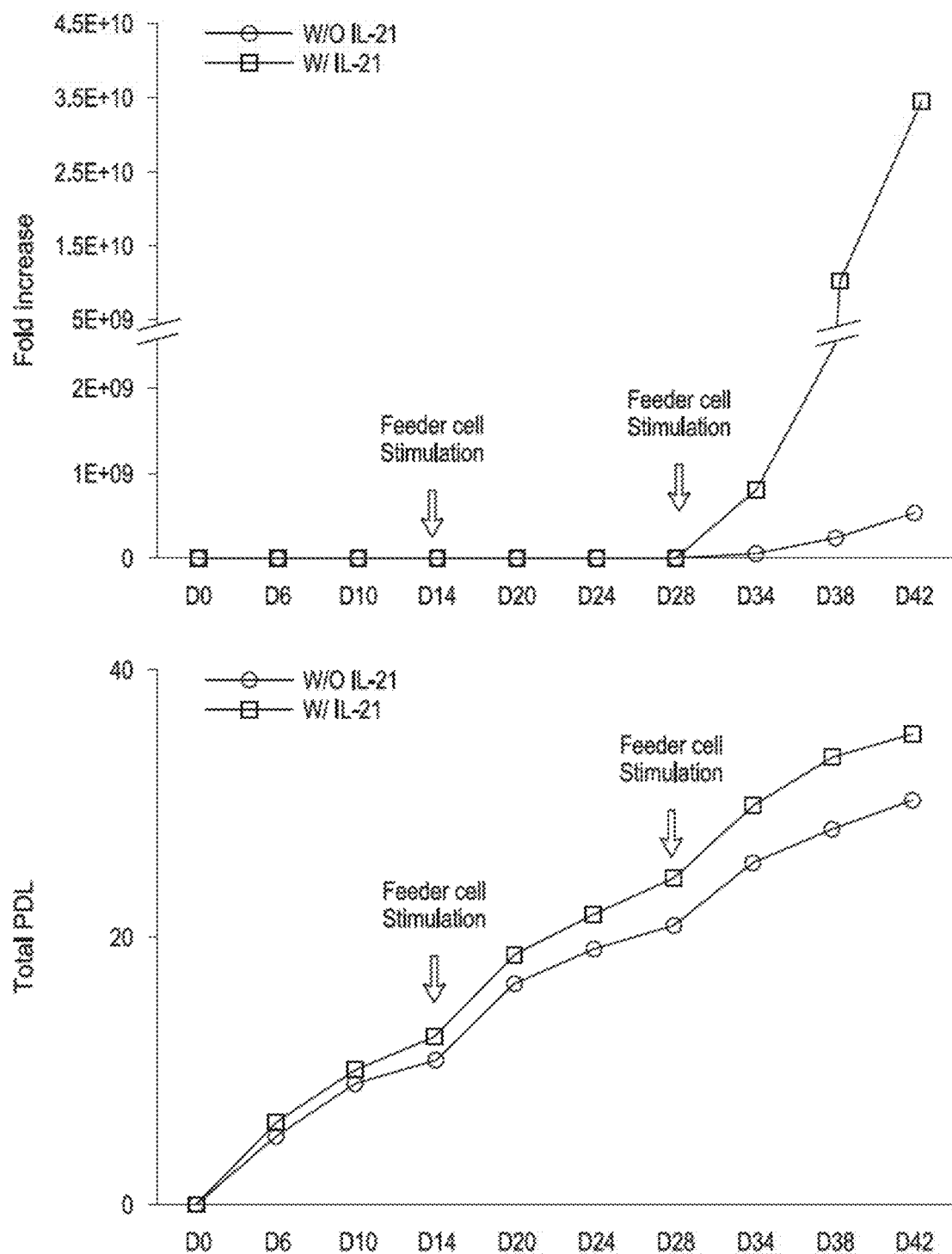
FIG. 9 illustrates graphs showing cell growth rates of NK cells with feeder cell stimulations.

As shown in FIG. 9, when treated with feeder cells twice or more and IL-21 together, the NK cells exhibited significantly increased expansion fold, and the NK cells treated with IL-21 exhibited greater expansion fold on Day 42, as compared with the NK cells not treated with IL-21 (approximately $3.4 \times 10^{10}$ vs. approximately $5.3 \times 10^{8}$).

Experimental Example 9. Confirmation of the Effect of Culturing of NK Cells Using Blood of Certain Cancer Patients CD56+ NK cells were produced according to the method of Example 1 for 17 days, except that PBMCs of colorectal cancer patients was used. The proliferative ability and the purity of the produced NK cells was measured using methods according to Experimental Examples 1 and 2.

For some groups, the NK cells were treated with IL-21 with a concentration of 50 ng/mL twice (Day 0 and Day 3 of culture), to confirm the effect of IL-21 treatment.

Figure 10A:
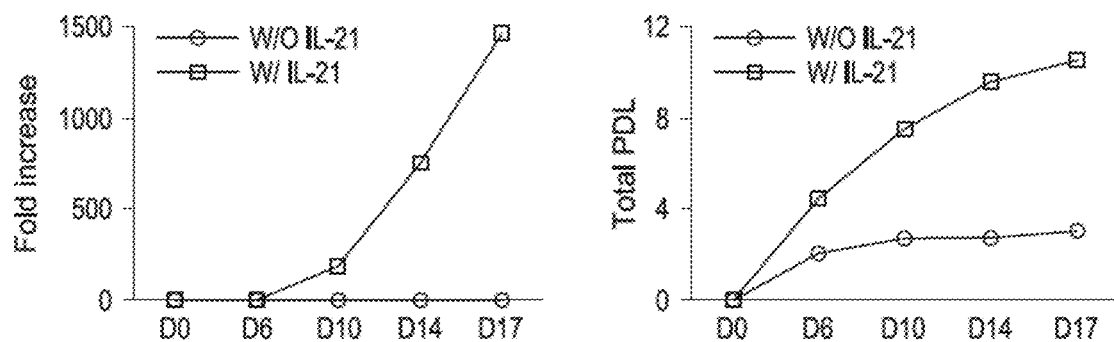
FIG. 10A illustrates graphs showing cell growth rates of NK cells produced from PBMCs of a cancer patient with or without treatment of IL-21.

As illustrated in FIG. 10A, the number of the NK cells not treated with IL-21 increased 8 times from Day 0, white when treated with IL-21, the number of the NK cells increased 1461 times from Day 0.

Figure 10B:
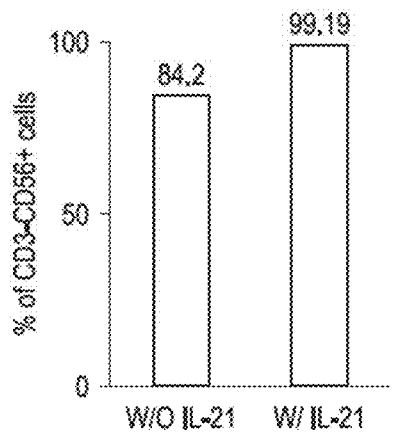
FIG. 10B illustrates a graph showing purity of CD3−/CD56+ NK cells produced from PBMCs of a cancer patient with or without treatment of IL-21.

Further, as illustrated in FIG. 10B, the purity of the NK cells not treated with IL-21 was only 84.2%, while when treated with IL-21, the purity of the NK cells was 99.19%.

Figure 10C:
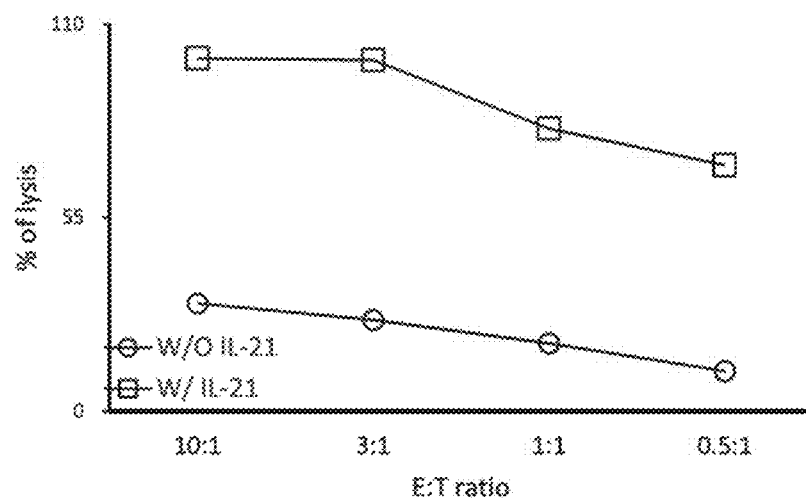
FIG. 10C illustrates a graph showing the short-term cytotoxicity of NK cells produced from PBMCs with or without treatment of IL-21 against K562 cells.

Further, the cytotoxicity of the NK cells treated with IL-21, and NK cells not treated with IL-21 against blood cancer cells (K562 cells, CCL-243™) were compared using the method according to Experimental Example 3. As illustrated in FIG. 10C, the NK cells treated with IL-21 exhibited greater anti-cancer activity as compared with the NK cells not treated with IL-21.

Figure 10D:
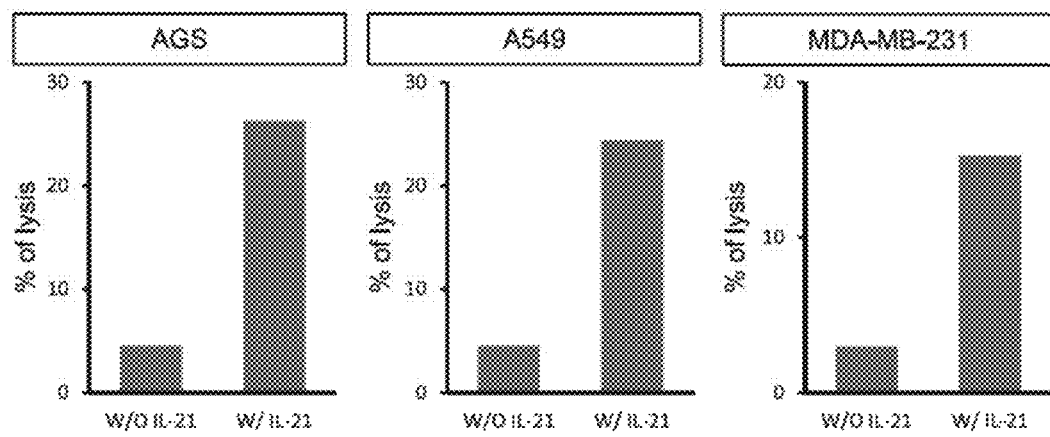
FIG. 10D illustrates graphs showing the long-term cytotoxicity of NK cells produced from PBMCs with or without treatment of IL-21 against AGS, A549, and MDA-MB-231 cells.

Also, Further, for each of the NK cells treated with IL-21, and NK cells not treated with IL-21, the cytotoxicity of the NK cells against solid tumor cells were compared using the method according to Experimental Example 3. AGS (stomach cancer, ATCC® CRL-1739™), A549 (lung cancer, ATCC® CRL-185™), and MDA-MB-231 (breast cancer, ATCC® HTB-26™) were used as solid tumor cell lines. As illustrated in FIG. 10D, the NK cells treated with IL-21 exhibited greater anti-cancer activity as compared with the NK cells not treated with IL-21.

Accordingly, by using methods as set forth herein, it may be possible to produce NK cells even for certain cancer patients who do not usually show an enough growth of NK cells.

Experimental Example 10. Confirmation of the Survival Rate of NK Cells in Therapeutic Composition With respect to each of the NK cells cultured in a $CO_2$ incubator according to Examples 1, 2 on Day 6 of culture, cells were inoculated into a 350 mL bag on the basis of the cell number of $1.0 \times 10^5$ to $2.0 \times 10^6$/mL and further cultured for 4 days. On Day 10 of culture, the cells were inoculated into a 1 L bag on the basis of the cell number of $1.0 \times 10^5$ to $2.0 \times 10^6$/mL and then further cultured for 4 days. Finally, on Day 14 of culture, the cells were inoculated into a 1 L bag on the basis of the cell number of $1.0 \times 10^5$ to $2.0 \times 10^6$/mL and then further cultured for 3 to 6 days.

The CD56+ NK cells on the 14th to 20th days of culture were washed three times and then suspended in a base compound (physiological saline and Hartman's solution) containing 1% albumin to be $2 \times 10^7$/mL. The cells were stored at 4° C. for 48 hours and then the cell survival rate was measured.

Further, in order to compare the effect of IL-2, the CD56+ NK cells were washed and suspended in a base compound containing 1% albumin (physiological saline, and Hartmann's solution or phosphate buffered saline), and then added with IL-2 at a concentration of 500 IU/mL. After being kept in 4° C. for 48 hours, cell survival rate was measured.

100 μL of each composition was taken to obtain a total of $2 \times 10^6$ CD56+ NK cells, washed once with 1 mL of the FACS staining buffer, centrifuged and suspended in 100 μL of an annex in V binding buffer. 5 μL of Annexin V-FITC and 5 μL of 7-AAD (Biolegend) were added in the suspension and mixed well, stored in a dark condition, and reacted at room temperature for 15 minutes, and then added with 400 μL of an Annexin V binding buffer before flow cytometry and mixed for 5 seconds. Thereafter, 10,000 to 100,000 cells per tube were obtained and analyzed. A cut-off was determined by setting a test tube which was not stained with the Annexin V-FITC and the 7-AAD as a negative control, and the survival rate was represented by a percentage of fraction of cells in which the Annexin V-FITC or the 7-AAD was negative.

Figure 11:
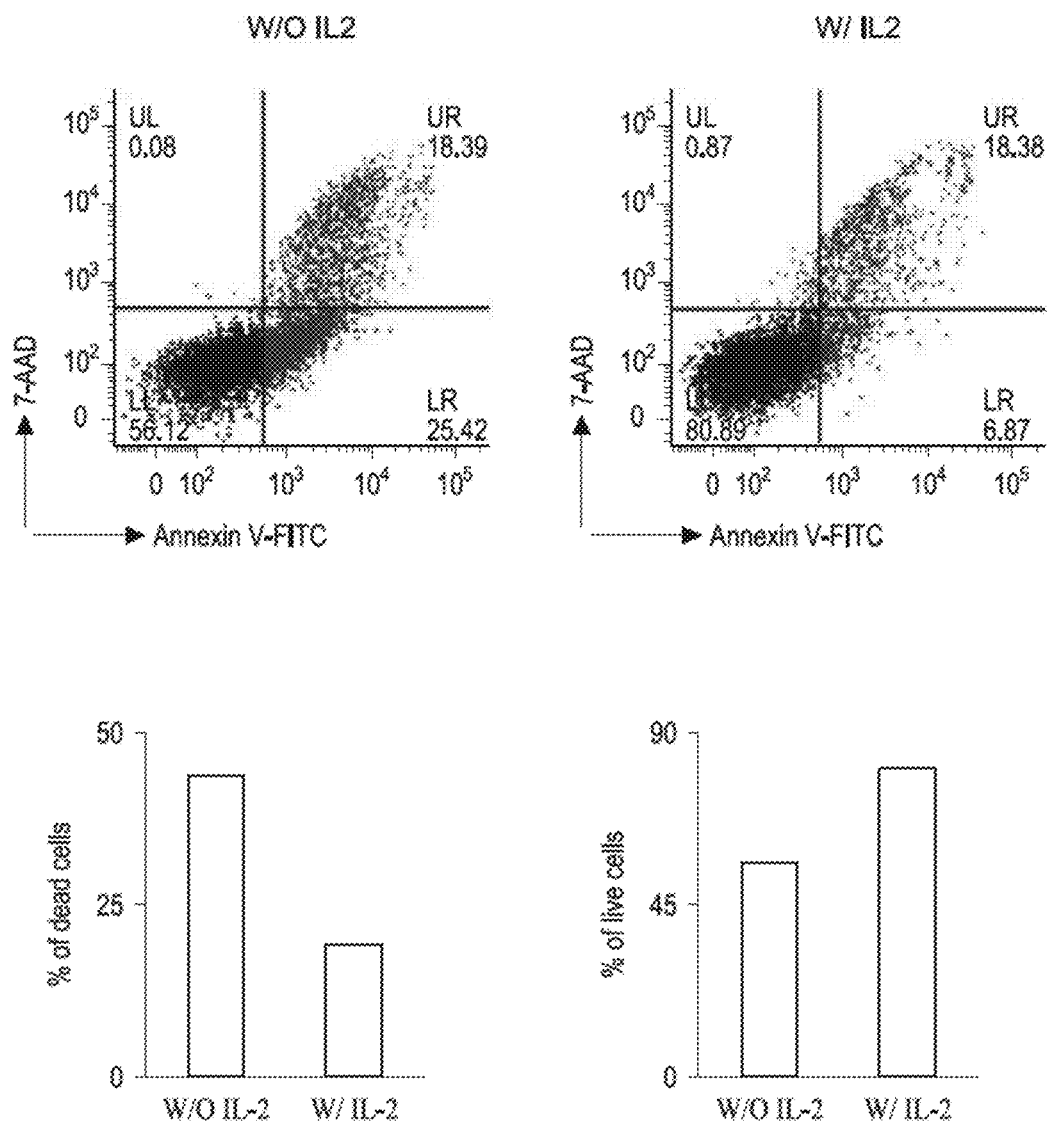
FIG. 11 illustrates graphs showing survival rate of NK cells treated with or without IL-2.

As illustrated in FIG. 11, when treated IL-2 (W/IL2), the apoptosis of the CD56+ NK cells was inhibited.

Experimental Example 11. Confirmation of the Cytotoxicity of NK Cells in Therapeutic Composition With respect to each of the NK cells cultured in a $CO_2$ incubator according to Examples 1, 2 on Day 6 of culture, cells were inoculated into a 350 mL bag on the basis of the cell number of $1.0 \times 10^5$ to $2.0 \times 10^6$/mL and further cultured for 4 days. On Day 10 of culture, the cells were inoculated into a 1 L bag on the basis of the cell number of $1.0 \times 10^5$ to $2.0 \times 10^6$/mL and then further cultured for 4 days. Finally, on Day 14 of culture, the cells were inoculated into a 1 L bag on the basis of the cell number of $1.0 \times 10^5$ to $2.0 \times 10^6$/mL and then further cultured for 3 to 6 days.

Before used in the experiment, the cancer cell lines were prepared by suspending under the following conditions, and sub-culturing at 37±1° C. at an interval of three days for 1 week or more:

CCRF-SB (blood cancer, ATCC® CCL-120™), AGS (stomach cancer, ATCC® CRL-1739™) and MIA-PACA2 (pancreatic cancer, ATCC® CRL-1420™): RPMI medium+ 10% FBS, SNU245 (cholangiocarcinoma, KCLB No. 00245), HCT15 (colon cancer, ATCC® CCL-225™) and NIH: OVCAR-3 (ovarian cancer, ATCC® HTB-161™): RPMI medium+10% FBS+25 mM HEPES, and MDA-MB-231 (breast cancer, ATCC® HTB-26™): DMEM medium+10% FBS.

The cancer cell lines (except for a blood cancer cell line) during culturing were detached from a culture dish using trypsin and suspended in the medium to be $5 \times 10^4$/mL, and then inoculated into a 24-well plate by 1 mL per well and attached for one day. To distinguish from the NK cells, the blood cancer cell line, which was a suspended culture cell, was labeled with green fluorescence, suspended in the medium to be $5 \times 10^4$/mL, and inoculated into a 24-well plate by 1 mL per well.

First in a 24-well plate inoculated with ACS (stomach cancer, ATCC® CRL-1739™), MIA-PACA2 (pancreatic cancer, ATCC® CRL-1420™), SNU245 (cholangiocarcinoma, KCLB No. 00245), HCT15 (colon cancer, ATCC® CCL-225™) and MDA-MB-231 (breast cancer, ATCC® HTB-26™) among the cancer cell lines, the CD56+ NK cells were added after one day to observe the cytotoxicity, and ratios of effector cells (CD56+ NK cells) and target cells (cancer cell lines) are shown in Table 7 below.

TABLE 7

| Effector:Target | Effector cell | Target cell |
| --- | --- | --- |
| 0:1 | 0 | $5 \times 10^4$ |
| 1:1 | $5 \times 10^4$ | $5 \times 10^4$ |
| 1:10 | $5 \times 10^3$ | $5 \times 10^4$ |
| 1:20 | $2.5 \times 10^3$ | $5 \times 10^4$ |

The plate inoculated with the effector cells and the target cells was cultured at 37±1° C. for 1 to 3 days, and at this time, in order to observe whether anti-cancer activity is increased by IL-2, 500 IU/ml of IL-2 was further added to an experimental group. In a negative control group, the CD56+ NK cells (effector cells) were not added and there was no anti-cancer activity reaction.

After 1 to 3 days of culture, the cells were washed with RPMI three times to remove the CD56+ NK cells present in the suspended form, and then the cancer cell lines remaining in the wells were detached using trypsin, stained with trypan blue and counted. Subsequently, the plate inoculated with the target cells and the effector cells was cultured at 37±1° C. for 1 to 3 days, and then the cells labeled with green fluorescence present in the 24 wells were counted using a flow cytometer.

The cytotoxicity for the cancer cell line was calculated using equation 2 below.

$$\text{Cytotoxicity} = \frac{\text{avg. number of fluorescence+ cells in wells with NK cells}}{\text{avg. number of fluorescence+ cells in wells with target cells only}} \times 100 \quad \text{Equation 2}$$

Figure 12:
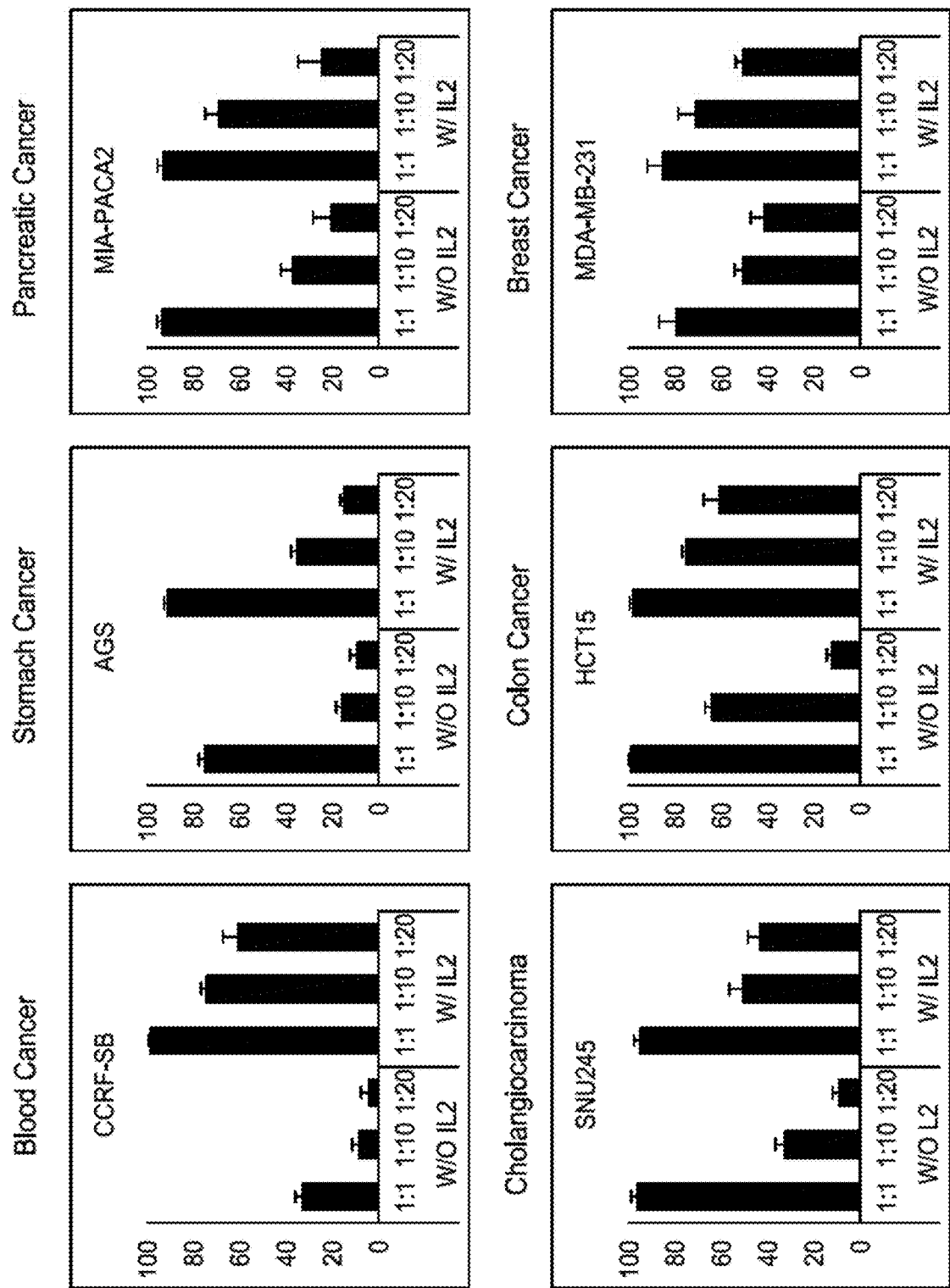
FIG. 12 illustrates graphs showing the cytotoxicity of NK cells treated with or without IL-2 against various cancer cells at various E:T ratios.

As a result, as illustrated in FIG. 12, it was confirmed that the cancer cell cytotoxicity was increased when IL-2 was treated together (W/IL2), as compared to when only the CD56+ NK cells were treated (W/O IL2).

Next, the CD56+ NK cells were added in the 24-well plate to which NIH:OVCAR-3 (ovarian cancer, ATCC® HTB-161™) cells was attached among the cancer cell lines to observe the cytotoxicity, and ratios of target cells (cancer cell lines) and effector cells (CD56+ NK cells) were shown in Table 8 below.

TABLE 8

| Effector:Target | Effector cells | Target cells |
| --- | --- | --- |
| 0:1 | 0 | $5 \times 10^4$ |
| 1:1 | $5 \times 10^4$ | $5 \times 10^4$ |

TABLE 8-continued

| Effector:Target | Effector cells | Target cells |
|---|---|---|
| 0.1:1 | $5 \times 10^3$ | $5 \times 10^4$ |
| 0.05:1 | $2.5 \times 10^3$ | $5 \times 10^4$ |

The plate inoculated with the effector cells and the target cells was cultured at 37±1° C. for 1 days, and, in order to observe whether anti-cancer activity is increased by IL-2, 500 IU/ml of IL-2 was further added to an experimental group. In a negative control group, the CD56+ NK cells were not added and there was no anti-cancer activity reaction.

After 1 day of culture, the cells were washed with RPMI three times to remove the CD56+ NK cells present in the suspended form, and then the cancer cell lines remaining in the wells were photographed using a camera.

Figure 13:
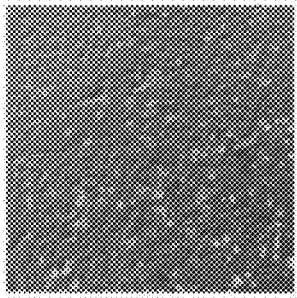
FIG. 13 illustrates photographs of remaining NIH:OVCAR-3 cells treated with NK cells treated with or without IL-2.

As a result, as illustrated in FIG. 13, the cancer cell cytotoxicity was increased when cancer cell lines were treated together with IL-2 (+IL2), as compared to when cancer cell lines were treated with only the CD56+ NK cells (−IL2).

Next, the CD56+ NK cells were added in the 24-well plate to which AGS (stomach cancer, ATCC® CRL-1739™) cells was attached among the cancer cell lines to observe the cytotoxicity, and ratios of target cells (cancer cell lines) and effector cells (CD56+ NK cells) were shown in Table 9 below.

TABLE 9

| Effector:Target | Effector cells | Target cells |
|---|---|---|
| 0:1 | 0 | $5 \times 10^4$ |
| 1:1 | $5 \times 10^4$ | $5 \times 10^4$ |
| 0.1:1 | $5 \times 10^3$ | $5 \times 10^4$ |
| 0.05:1 | $2.5 \times 10^3$ | $5 \times 10^4$ |

The plate inoculated with the effector cells and the target cells was cultured at 37±1° C. for 1 days, and, in order to observe whether anti-cancer activity is increased by IL-2, 500 IU/ml of IL-2 was further added to an experimental group. In a negative control group, the CD56+ NK cells were not added and there was no anti-cancer activity reaction.

After 1 day of culture, the cells were washed with RPMI three times to remove the CD56+ NK cells present in the suspended form, and then the cancer cell lines remaining in the wells were photographed using a camera.

Figure 14:
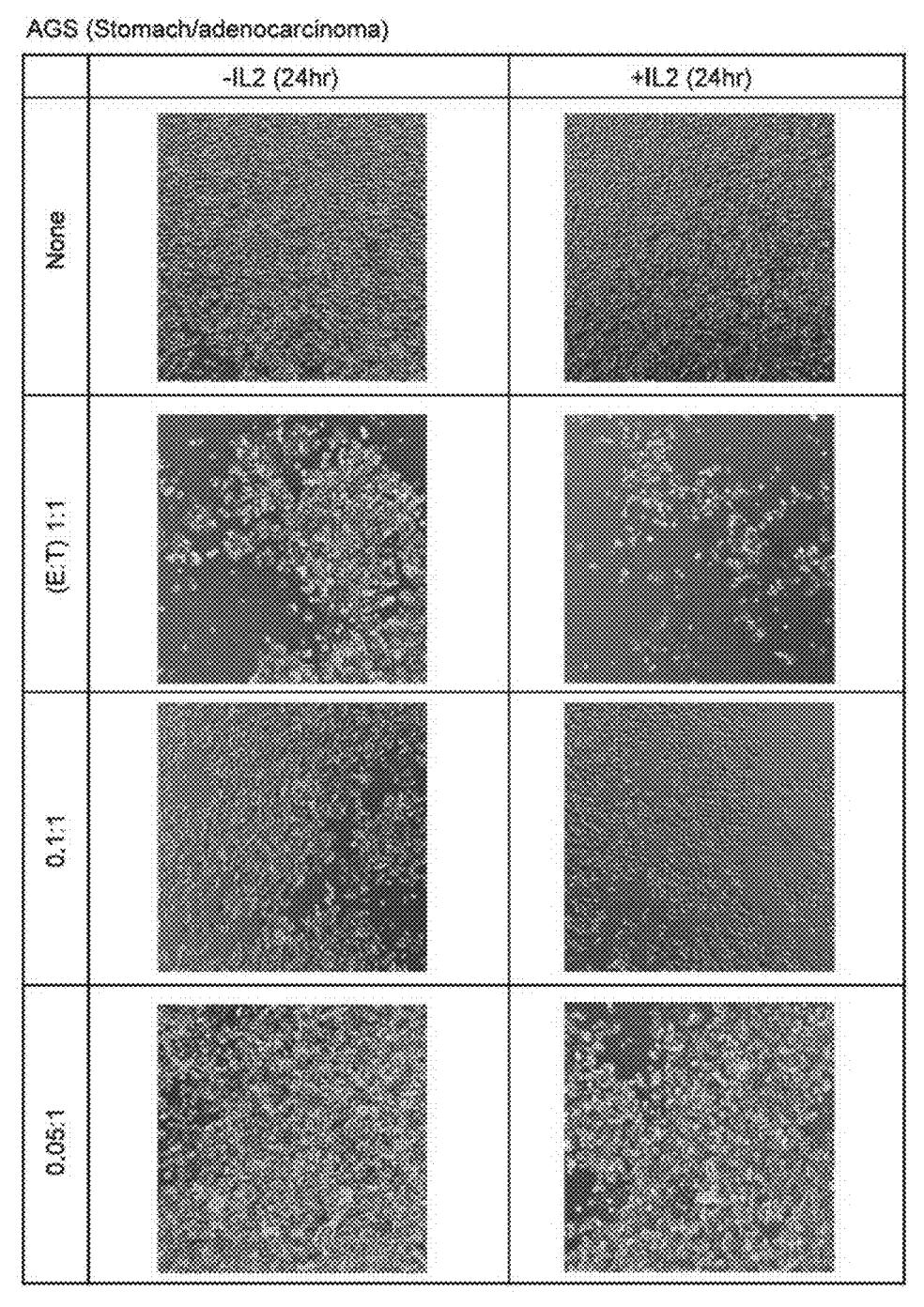

As a result, as illustrated in FIG. 14, the cancer cell cytotoxicity was increased when cancer cell lines were treated together with IL-2 (+IL2), as compared to when cancer cell lines were treated with only the CD56+ NK cells (−IL2).

Experimental Example 12. Confirmation of Anticancer Effect of NK Cells in Animal Models CD56+ NK cells are produced according to the method of Examples 1, 2 and Comparative Examples 1, 2 for 17 days, except that PBMCs of colorectal cancer patients is used. With respect to each of the NK cells cultured in a $CO_2$ incubator according to Examples 1, 2 and Comparative Examples 1, 2, on Day 6 of culture in a T 25 culture flask, cells are inoculated into a 350 mL bag on the basis of the cell number of $1.0 \times 10^5$ to $2.0 \times 10^6$/mL and further cultured for 4 days. On Day 10 of culture, the cells are inoculated into a 1 L bag on the basis of the cell number of $1.0 \times 10^5$ to $2.0 \times 10^6$/ml, and then further cultured for 4 days. Finally, on Day 14 of culture, the cells are inoculated into a 1 L bag on the basis of the cell number of $1.0 \times 10^5$ to $2.0 \times 10^6$/mL and then further cultured for 3 to 6 days.

Animal models of human cancer are constructed by xenograft of human cancer cell line into mice. Following human cancer cell lines are used: AGS (stomach cancer), MIA-PACA2 (pancreatic cancer), SNU245 (cholangiocarcinoma), HCT15 (colon cancer) and NIH:OVCAR-3 (ovarian cancer), and MDA-MB-231 (breast cancer). After xenograft of cancer, the mice are grouped randomly and marked. The control group is injected 200 µL of Hartmann's solution into the vein of tail. The NK cell-treated (+IL-2) group is injected five times with $1 \times 10^7$ NK cells/200 µL and 500 IU/mL of IL-2 at 2-3-day intervals from 1 week after xenograft of cancers into the vein of tail. The NK cell-treated (−IL-2) group is injected five times with $1 \times 10^7$ NK cells/200 µL at 2-3-day intervals from 1 week after xenograft of cancers into the vein of tail.

To follow up tumor growth, during the study period, mice are tested for body weight and tumor volume three time a week. Length of major axis and minor axis are measured using a caliper and tumor volume is determined according to the following equation (Equation 3).

Tumor Volume (mm$^3$)=(length of major axis (mm))× (length of minor axis (mm))$^2$×0.5     Equation 3

The NK cell-treated (−IL-2) group exhibits a reduction in tumor growth after 8 weeks treatment of approximately 50% compared to the control group based on luciferase images for each cancer type. The NK cell-treated (+IL-2) group exhibits a further reduction in tumor growth of approximately 60% compared to the control group for each cancer type.

Experimental Example 13. Confirmation of Anticancer Effect of NK Cells in Cancer Patients CD56+ NK cells are produced according to the method of Examples 1, 2 and Comparative Examples 1, 2 for 18 days, except that PBMCs of colorectal cancer patients is used. With respect to each of the NK cells cultured in a $CO_2$ incubator according to Examples 1, 2 and Comparative Examples 1, 2, on Day 6 of culture in a T 25 culture flask, cells are inoculated into a 350 mL bag on the basis of the cell number of $1.0 \times 10^5$ to $2.0 \times 10^6$/mL and further cultured for 4 days. On Day 10 of culture, the cells are inoculated into a 1 L bag on the basis of the cell number of $1.0 \times 10^5$ to $2.0 \times 10^6$/mL and then further cultured for 4 days. Finally, on Day 14 of culture, the cells are inoculated into a 1 L bag on the basis of the cell number of $1.0 \times 10^5$ to $2.0 \times 10^6$/mL and then further cultured for 3 to 6 days.

The colorectal cancer patients are grouped randomly and marked. The control group is not injected with NK cells. The NK cell-treated (+IL-2) group is injected three times with $1-3 \times 10^7$ NK cells/per kg of body weight and 500 IU/mL of IL-2 at six week intervals intravenously. The NK cell-treated (−IL-2) group is injected six times with $1-3 \times 10^7$ NK cells/per kg of body weight at six week intervals intravenously.

Tumor growth is monitored at 1, 3, 6, 12 months. After 12 months, the NK cell-treated (−IL-2) group exhibits overall decrease in tumor size, and the NK cell-treated (+IL-2) group exhibits further overall decrease in tumor size.

Experimental Example 14. Confirmation of Anticancer Effect of NK Cells in Alzheimer's Disease Patients CD56+ NK cells are produced according to the method of Examples 1, 2 and Comparative Examples 1, 2 for 18 days, except that PBMCs of colorectal cancer patients is used. With respect to each of the NK cells cultured in a $CO_2$ incubator according to Examples 1, 2 and Comparative Examples 1, 2, on Day 6 of culture in a T 25 culture flask, cells are inoculated into a 350 mL bag on the basis of the cell number of $1.0 \times 10^5$ to $2.0 \times 10^6$/mL and further cultured for 4 days. On Day 10 of culture, the cells are inoculated into a 1 L bag on the basis of the cell number of $10 \times 10^5$ to $2.0 \times 10^6$/mL and then further cultured for 4 days. Finally, on Day 14 of culture, the cells are inoculated into a 1 L bag on the basis of the cell number of $1.0 \times 10^5$ to $2.0 \times 10^6$/mL and then further cultured for 3 to 6 days.

Alzheimer's Disease patients are grouped randomly and marked. The control group is not injected with NK cells. The NK cell-treated group is injected six times with $1-3 \times 10^7$ NK cells/per kg of body weight and 500 IU/mL of IL-2 at weekly intervals intravenously.

Cognitive function of the patient are monitored at 1, 3, 6, 12 months. After 12 months, the NK cell-treated group exhibits improved cognitive function.

Experimental Example 15. Confirmation of Anticancer Effect of NK Cells in Autoimmune Disease Patients CD56+ NK cells are produced according to the method of Examples 1, 2 and Comparative Examples 1, 2 for 18 days, except that PBMCs of colorectal cancer patients is used. With respect to each of the NK cells cultured in a $CO_2$ incubator according to Examples 1, 2 and Comparative Examples 1, 2, on Day 6 of culture in a T 25 culture flask, cells are inoculated into a 350 mL bag on the basis of the cell number of $1.0 \times 10^5$ to $2.0 \times 10^6$/mL and further cultured for 4 days. On Day 10 of culture, the cells are inoculated into a 1 L bag on the basis of the cell number of $1.0 \times 10^5$ to $2.0 \times 10^6$/mL and then further cultured for 4 days. Finally, on Day 14 of culture, the cells are inoculated into a 1 L bag on the basis of the cell number of $1.0 \times 10^6$ to $2.0 \times 10^6$/mL and then further cultured for 3 to 6 days.

Multiple sclerosis patients are grouped randomly and marked. The control group is not injected with NK cells. The NK cell-treated group is injected six times with $1-3 \times 10^7$ NK cells/per kg of body weight and 500 IU/mL of IL-2 at weekly intervals intravenously.

Cognitive function of the patient are monitored at 1, 3, 6, 12 months. After 12 months, the NK cell-treated group exhibits improved cognitive function.

Terminology

The foregoing description of the exemplary embodiments has been presented only for the purposes of illustration and description and is not intended to be exhaustive or to limit the invention to the precise forms disclosed. Many modifications and variations are possible in light of the above teaching. It is contemplated that various combinations or sub combinations of the specific features and aspects of the embodiments disclosed above may be made and still fall within one or more of the inventions. Further, the disclosure herein of any particular feature, aspect, method, properly, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof.

The embodiments were chosen, and described in order to explain the principles of the invention and their practical application so as to activate others skilled in the art to utilize the invention and various embodiments and with various modifications as are suited to the particular use contemplated. Alternative embodiments will become apparent to those skilled in the act to which the invention is defined by the appended claims rather than the foregoing description and the exemplary embodiments described therein.

Conditional language, such as "can," "could," "might" or "may," unless specifically stated otherwise, or otherwise understood within the context as used, is generally intended to convey that certain, embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the terms "or" is used in its inclusive sense (and not in its exclusive sense) so that when used, for example, to connect a list of elements, the term "or" means one some, or all of the elements in the list.

The ranges disclosed herein also encompass any and all overlap, sub-ranges, and combinations thereof. Language such as "up to," "at least," "greater than," "less than," "between," and the like includes the number recited.

Numbers preceded by a term such as "approximately", "about" and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

The term "generally" as used herein represents a value, amount, or characteristic that predominantly includes or tends toward a particular value, amount, or characteristic. As an example, in certain embodiments, the term "generally uniform" refers to a value, amount, or characteristic that departs from exactly uniform by less than 20%, less than 15%, less than 10%, less than 5%, less than 1%, less than 0.1%, and less than 0.01%.

The ranges disclosed herein also encompass any and all overlap, sub-ranges, and combinations thereof. Language such as "up to" "at least" "greater than" "less than,"

"between" and the like includes the number recited. Numbers preceded by a term such as "about" or "approximately" include the recited numbers. For example, "about 5.0 cm" includes "5.0 cm."

Some embodiments have been described in connection with schematic drawings. However, it should be understood that the schematic drawings are not drawn to scale. Distances are merely illustrative and do not necessarily bear an exact relationship to actual dimensions and layout of the devices illustrated.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method of expanding natural killer cells in culture, comprising:
    isolating peripheral blood mononuclear cells (PBMCs) from a blood sample;
    isolating at least one of CD56+ cells and/or CD3−/CD56+ cells from the PBMCs; and
    co-culturing the at least one of CD56+ cells and/or CD3−/CD56+ cells with a combination of feeder cells in the presence of at least two cytokines;
    wherein the combination of feeder cells comprises irradiated Jurkat cells and irradiated Epstein-Barr virus transformed lymphocyte continuous line (EBV-LCL) cells,
    wherein the at least two cytokines comprise IL-2 and IL-21.

2. The method of claim 1, wherein isolating at least one of CD56+ cells and/or CD3−/CD56+ cells from the PBMCs is conducted by using at least one of CD56 microbeads and CD3 microbeads.

3. The method of claim 1, wherein the at least two cytokines further comprise one or more cytokines selected from a group consisting of IL-15, Flt3-L, SCF, IL-7, IL-18, IL-4, type I interferons, GM-CSF, IGF 1, and combinations thereof.

4. The method of claim 1, wherein IL-2 is added at a concentration of 50-1000 IU/mL.

5. The method of claim 1, wherein IL-21 is added at a concentration of 10-100 ng/mL.

6. The method of claim 1, wherein the ratio of the irradiated Jurkat cells and the irradiated EBV-LCL cells is about 1:0.1-5 or 0.1-5:1.

7. The method of claim 1, wherein the co-culturing comprises co-culturing for 1-50 days.

8. The method of claim 1, further comprising:
    co-culturing the at least one of CD56+ cells and/or CD3−/CD56+ cells with the combination of feeder cells, in the presence of IL-2 for a first period; and
    co-culturing the at least one of CD56+ cells and/or CD3−/CD56+ cells with the combination of feeder cells, in the presence of IL-21 for a second period.

9. The method of claim 8, wherein IL-21 is added more than once during Day 0-6 of the second period.

10. The method of claim 8, wherein IL-21 and the combination of feeder cells are added more than once during Day 0-6 of the second period.

11. The method of claim 8, wherein IL-21 is added more than once during the first six days of every fourteen-day cycle during the second period.

12. The method of claim 1, wherein the at least one of CD56+ cells and/or CD3−/CD56+ cells and the combination of feeder cells is co-cultured with a ratio of about 1:1-100 of CD56+ cells and/or CD3−/CD56+ cells to feeder cells.

13. A composition made by the method of claim 1.

14. A method of expanding natural killer cells in culture, comprising:
    isolating peripheral blood mononuclear cells (PBMCs) from a blood sample;
    isolating at least one of CD56+ cells and/or CD3−/CD56+ cells from the PBMCs; and
    co-culturing the at least one of CD56+ cells and/or CD3−/CD56+ cells with a combination of feeder cells in the presence of at least two cytokines;
    wherein the combination of feeder cells comprises irradiated Jurkat cells and irradiated Epstein-Barr virus transformed lymphocyte continuous line (EBV-LCL) cells,
    wherein the at least two cytokines comprise IL-2 and IL-21, and
    wherein both the feeder cells and the cytokines are supplemented at intervals throughout the expansion in culture.

15. The method of claim 14, wherein isolating at least one of CD56+ cells and/or CD3−/CD56+ cells from the PBMCs is conducted by using at least one of CD56 microbeads and CD3 microbeads.

16. The method of claim 14, wherein IL-21 is added at a concentration of 10-100 ng/mL.

17. The method of claim 14, wherein IL-21 is added once or more during each of the following periods: Day 0-6; Day 14-20; and Day 28-34.

18. The method of claim 14, wherein the co-culturing comprises co-culturing for 1-50 days.

* * * * *

UNITED STATES PATENT AND TRADEMARK OFFICE
CERTIFICATE OF CORRECTION

PATENT NO. : 10,590,385 B2  
APPLICATION NO. : 16/523964  
DATED : March 17, 2020  
INVENTOR(S) : Sang Woo Park et al.

Page 1 of 4

It is certified that error appears in the above-identified patent and that said Letters Patent is hereby corrected as shown below:

On the Title Page

Column 2, Item (56), Line 5, under Other Publications, delete "Sustrained" and insert --Sustained--.

On Page 2, Column 1, Item (56), Lines 2-3, under Other Publications, delete "transplantation"Nature" and insert --transplantation" Nature--.

On Page 2, Column 1, Item (56), Line 15, under Other Publications, delete "Feasibllity" and insert --Feasibility--.

On Page 2, Column 1, Item (56), Line 16, under Other Publications, delete "Myelold Leukema," and insert --Myeloid Leukemia,--.

On Page 2, Column 2, Item (56), Line 5, under Other Publications, delete "CD8$_+$" and insert --CD8$^+$--.

In the Drawings

On Sheet 5 of 17, FIG. 4B, Line 5 (Approx.), delete "PBCM" and insert --PBMC--.

On Sheet 5 of 17, FIG. 4B, Line 5 (Approx.), delete "PBCM" and insert --PBMC--.

On Sheet 5 of 17, FIG. 4B, Line 5 (Approx.), delete "PBCM" and insert --PBMC--.

On Sheet 5 of 17, FIG. 4B, Line 5 (Approx.), delete "PBCM" and insert --PBMC--.

On Sheet 5 of 17, FIG. 4B, Line 5 (Approx.), delete "PBCM" and insert --PBMC--.

On Sheet 5 of 17, FIG. 4B, Line 5 (Approx.), delete "PBCM" and insert --PBMC--.

On Sheet 15 of 17, FIG. 12, Line 10 (Approx.), delete "W/O L2" and insert --W/O IL2--.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,590,385 B2

In the Specification

In Column 1, Lines 44-45, delete "(Bauernhofer" and insert --(Bauemhofer--.

In Column 1, Line 45, delete "Immunol." and insert --Immunol.,--.

In Column 1, Line 45, delete "33;" and insert --33:--.

In Column 1, Line 49, delete "Jo" and insert --to--.

In Column 1, Line 55, delete "small" and insert --small,--.

In Column 2, Line 35, delete "CD-/CD56+" and insert --CD3-/CD56+--.

In Column 3, Line 45, delete "CD564" and insert --CD56+--.

In Column 3, Line 55, delete "rales" and insert --rates--.

In Column 5, Line 4, delete "IFN-a," and insert --IFN-α,--.

In Column 5, Line 4, delete "IFN-b," and insert --IFN-β,--.

In Column 5, Line 59, delete "CliniMACSs," and insert --CliniMACS,--.

In Column 6, Line 52, delete "Line" and insert --line--.

In Column 6, Line 53, delete "invest," and insert --Invest,--.

In Column 6, Line 60, delete "9 ml," and insert --9 mL--.

In Column 7, Line 27, delete "step")" and insert --step").--.

In Column 7, Line 43, delete "of" and insert --or--.

In Column 8, Line 20, delete "IU/mL" and insert --IU/mL.--.

In Column 10, Line 7, delete "interval the" and insert --interval. The--.

In Column 10, Line 16 (Approx.), delete "IU/ml." and insert --IU/mL.--.

In Column 11, Line 12 (Approx.), delete "Preparation," and insert --Preparation--.

In Column 11, Line 38, delete "Alter" and insert --After--.

In Column 11, Line 63, delete "PBMCS" and insert --PBMCs--.

CERTIFICATE OF CORRECTION (continued)
U.S. Pat. No. 10,590,385 B2

In Column 11, Line 64, delete "PBS" and insert --FBS--.

In Column 12, Line 2, delete "(OBV" and insert --(EBV--.

In Column 12, Line 27 (Approx.), delete "CP56+" and insert --CD56+--.

In Column 12, Line 39 (Approx.), delete "CP56+" and insert --CD56+--.

In Column 12, Line 47 (Approx.), delete "CP56+" and insert --CD56+--.

In Column 12, Line 54 (Approx.), delete "Continuation" and insert --Confirmation--.

In Column 12, Line 61, delete "$10^6$" and insert --$10^5$--.

In Column 13, Line 18, delete "papulation" and insert --population--.

In Column 13, Line 39, delete "purify" and insert --purity--.

In Column 13, Line 51, delete "Continuation" and insert --Confirmation--.

In Column 14, Line 14 (Approx.), delete "respectively, in" and insert --respectively. In--.

In Column 14, Line 33, delete "1000" and insert --1,000--.

In Column 14, Line 62 (Approx.), delete "CD56" and insert --CD56+--.

In Column 15, Line 1, delete "(king cancer." and insert --(lung cancer,--.

In Column 15, Line 6, delete "Inc.)" and insert --Inc.),--.

In Column 15, Line 26 (Approx.), delete "group)." and insert --group),--.

In Column 15, Line 27 (Approx.), delete "group). Of" and insert --group), or--.

In Column 15, Line 32 (Approx.), delete "10:" and insert --10;--.

In Column 15, Line 55, delete "group)." and insert --group),--.

In Column 15, Line 63, delete "11-21" and insert --IL-21--.

In Column 16, Line 23 (Approx.), delete "told" and insert --fold--.

In Column 16, Line 39 (Approx.), delete "group)." and insert --group),--.

In Column 16, Line 39 (Approx.), delete "group)." and insert --group),--.

CERTIFICATE OF CORRECTION (continued)
U.S. Pat. No. 10,590,385 B2

In Column 17, Line 6, delete "ail" and insert --all--.

In Column 17, Line 21, delete "TL-21:" and insert --IL-21:--.

In Column 17, Line 39, delete "5A," and insert --8A,--.

In Column 18, Line 26, delete "white" and insert --while--.

In Column 19, Line 18 (Approx.), delete "annex in" and insert --annexin--.

In Column 20, Line 4, delete "First" and insert --First,--.

In Column 20, Line 4, delete "ACS" and insert --AGS--.

In Column 20, Line 26 (Approx.), delete "IU/ml" and insert --IU/mL--.

In Column 20, Line 40, delete "equation" and insert --Equation--.

In Column 20, Line 48 (Approx.), delete "wells" and insert --well--.

In Column 21, Line 11 (Approx.), delete "IU/ml" and insert --IU/mL--.

In Column 21, Line 42, delete "IU/ml" and insert --IU/mL--.

In Column 22, Line 2, delete "ml," and insert --mL--.

In Column 23, Line 8, delete "10" and insert --1.0--.

In Column 23, Line 38, delete "$10^6$" and insert --$10^5$--.

In Column 23, Line 60, delete "properly," and insert --property,--.

In Column 24, Line 24, delete "act" and insert --art--.

In Column 24, Line 27, delete ""might"" and insert --"might,"--.

In Column 24, Line 38, delete "terms" and insert --term--.

In Column 24, Line 41, delete "one" and insert --one,--.

In Column 24, Line 48, delete ""about"" and insert --"about",--.

In Column 24, Line 67, delete ""up to" "at least" "greater than"" and insert --"up to," "at least," "greater than,"--.